(12) United States Patent
Harima

(10) Patent No.: US 7,123,019 B2
(45) Date of Patent: Oct. 17, 2006

(54) POLAROGRAPHIC DENSITOMETER

(75) Inventor: Shinichi Harima, Daisen (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 11/136,576

(22) Filed: May 25, 2005

(65) Prior Publication Data
US 2005/0285599 A1 Dec. 29, 2005

(30) Foreign Application Priority Data
Jun. 23, 2004 (JP) ............................. 2004-185484

(51) Int. Cl.
G01N 27/62 (2006.01)
G01R 27/08 (2006.01)
(52) U.S. Cl. ..................... 324/464; 324/713; 399/74
(58) Field of Classification Search ............... 324/464, 324/713; 399/74
See application file for complete search history.

(56) References Cited

U.S. PATENT DOCUMENTS 4,950,378 A * 8/1990 Nagata ................. 204/403.11
5,781,455 A * 7/1998 Hyodo ................. 204/403.11

FOREIGN PATENT DOCUMENTS

JP 2002-214220 7/2002

* cited by examiner

Primary Examiner—Vincent Q. Nguyen
Assistant Examiner—Timothy J. Dole
(74) Attorney, Agent, or Firm—McDermott Will & Emery LLP

(57) ABSTRACT

A polarographic densitometer has a voltage applying circuit, a sensor unit, an impedance reduction circuit, and a current/density conversion unit. The voltage applying circuit applies specified voltage, and the sensor unit includes a group of electrodes to produce a current output in response to any reaction caused in a specimen when the specified voltage is applied by the voltage applying circuit. Furthermore, the impedance reduction circuit reduces impedance of the specimen between the electrodes of the group, and the current/density conversion unit converts the current output of the sensor unit when the impedance is reduced by the impedance reduction circuit into the density of specific material in the specimen.

12 Claims, 19 Drawing Sheets

POLAROGRAPHIC DENSITOMETER

BACKGROUND OF THE INVENTION

1. Field of the Invention

The present invention relates to a polarographic densitometer for measuring the density of ions or gas components of the specimen in liquid or vapor phase.

2. Prior Art

Previously known in the art as a kind of densitometer for measuring the density of ions or gas components in specimen when it is in liquid or vapor phase is a chlorine meter in which a pair of electrodes is provided each made up of different metals, said electrodes are immersed in the liquid specimen and the residual chlorine is reduced on the surfaces of the electrodes to develop an electro-motive force between the electrodes, on the basis of which the density of chlorine in the liquid is determined (refer to e.g. Patent Document 1).

The chlorine meter as disclosed in Patent Document 1 includes a pair of electrodes: one is made up of a platinum wire and the other is a silver wire. The silver wire electrode is provided with a silver chloride coating at such portion thereof that is to be immersed in the liquid. The pair of electrodes forms a sensor which is immersed in the liquid specimen (e.g. tap water) to allow chlorine in the liquid to be reduced at the surfaces of the electrodes. Then, electric current flows between the electrodes to develop an electro-motive force in proportion to the density of chlorine in the liquid, on the basis of which the density of chlorine is determined.

Patent Document 1: Japanese Patent Laid-Open No. 2002-214220

However, the chlorine meter, as described above, is defective in that due to instability in reaction between the metal electrode and the liquid under test there is less repeatability and linearity provided in relation between potential on the electrodes and the density of certain material and it takes longer period of time for performing measurement.

In view of the above an object of the present invention is to solve the problems in the prior art, as described above, and to provide an improved polarographic densitometer having capability of measuring with higher precision, in reduced time and with highly effective.

SUMMARY OF THE INVENTION

In order to attain such object the present invention provides, in one aspect, a polarographic densitometer, comprising: a voltage applying circuit; a sensor unit; an impedance reduction circuit; and a current/density conversion unit, wherein said voltage applying circuit applies specified voltage, said sensor unit includes a group of electrodes to produce a current output in response to any reaction caused in a specimen when the specified voltage is applied by said voltage applying circuit, said impedance reduction circuit reduces impedance of the specimen between said electrodes of the group, and said current/density conversion unit converts the current output of said sensor unit when the impedance is reduced by said impedance reduction circuit into the density of specific material in the specimen.

According to one embodiment of the present invention, if the specimen is liquid, the densitometer further comprises an electric conductivity measurement unit, said conductivity measurement unit measures the electric conductivity of the liquid specimen between any of electrodes of the group, and said current/density conversion unit converts the current output of said sensor unit in proportion to the electric conductivity measured by said electric conductivity measurement unit into the density of specific material in the liquid specimen.

According to another embodiment of the present invention, if the specimen is liquid, the densitometer further comprises: an immersion measurement unit; and an impedance reduction circuit switching unit, wherein said immersion measurement unit determines that said sensor unit is immersed in the liquid between any of the electrodes of the group within a standby interval before said current/density conversion unit starts to convert the current output into the density of specific material, and the impedance reduction circuit switching unit switches the impedance reduction circuit to no-connection mode for a period during which determination is done by said immersion measurement unit within the standby interval.

According to further embodiment of the present invention, said group of electrodes consists of a counter/reference electrode to which the specified voltage is applied by said voltage applying circuit and a plurality of working electrodes each having different area to produce the current in response to any reaction caused in the specimen in conjunction with said counter/reference electrode, said impedance reduction circuit reduces the impedance of the specimen between said counter/reference electrode and each of said working electrodes, and a working electrode switching unit is provided for switching the connection of the plurality of working electrodes in such order that the working electrode having the smallest area is initially connected.

According to yet further embodiment of the present invention, said group of electrodes consists of a reference electrode by which a reference voltage is developed in the specimen for providing the specified voltage output from said voltage applying circuit, a counter electrode to which the specified voltage output from said voltage applying circuit is applied, and a plurality of working electrodes each having different area to produce the current in response to any reaction caused in the specimen in conjunction with said counter/reference electrode, said impedance reduction circuit reduces the impedance of the specimen between said counter electrode and each of said working electrodes, and a working electrode switching unit is provided for switching the connection of the plurality of working electrodes in such order that the working electrode having the smallest area is initially connected.

According to yet further embodiment of the present invention, said voltage applying circuit includes a voltage follower to which a basic voltage for said group of electrodes to only react with specific material of the specimen is input and from which the specified voltage is output, and said group of electrodes consists of a counter/reference electrode to which the specified voltage is applied from the output of said voltage follower and a working electrode for providing the current in response to any reaction caused in the specimen in conjunction with said counter/reference electrode.

According to yet further embodiment of the present invention, said voltage applying circuit includes a voltage follower to which a basic voltage for said group of electrodes to only react with specific material of the specimen is input and from which the specified voltage is output, and said group of electrodes consists of a reference electrode by which a reference voltage is developed in the specimen for providing the specified voltage output from said voltage applying circuit, a counter electrode to which the specified voltage output from said voltage follower is applied, and a working electrode for providing the current in response to any reaction caused in the specimen in conjunction with said counter electrode.

According to yet further embodiment of the present invention, said voltage applying circuit includes a potentiostat to which a basic voltage for said group of electrodes to only react with specific material of the specimen and a reference voltage developed in the specimen are input and from which the specified voltage is output, and said group of electrodes consists of a reference electrode by which a reference voltage is developed in the specimen for providing the specified voltage output from said voltage applying circuit, a counter electrode to which the specified voltage output from said potentiostat is applied, and a working electrode for providing the current in response to any reaction caused in the specimen in conjunction with said counter/reference electrode.

According to yet further embodiment of the present invention, the densitometer further comprises an offset current calibration unit, said calibration unit calibrates any offset current that may be caused when the specified voltage is applied by said voltage applying circuit.

According to yet further embodiment of the present invention, the densitometer further comprises: a current amplifier circuit; and an amplifying factor control unit, wherein said current amplifier circuit amplifies the current output from the sensor when the impedance is reduced by said impedance reduction circuit, and said amplifying factor control unit controls the amplifying factor for the current from said current amplifier circuit.

According to yet further embodiment of the present invention, said voltage applying circuit applies the specified voltage that is variable, and the densitometer further comprises: a selection unit; and a specified voltage controller unit, wherein said selection unit selects any density of specific material from among a plurality of densities, and said specified voltage controller unit provides variable control to produce such specified voltage from said voltage applying circuit that causes reaction of said group of electrodes with the specimen in proportion to the density of specific material selected by said selection unit.

Effects of the Invention:

A polarographic densitometer according to the present invention is operated in such manner that an electric current is produced in a sensor unit due to reaction in proportion to the density of specific material in specimen, while reducing the impedance of the specimen between electrodes of an electrode group in an impedance reduction circuit, and then, a current/density converter converts the electric current into the density of specific material in the specimen. In particular, the electric current flows through the impedance reduction circuit so that the impedance between the electrodes is reduced, making the reaction more stable. Accordingly, the present invention is advantageous in that the linearity and repeatability is enhanced and the time period for measurement is shortened.

Furthermore, in the polarographic densitometer according to the present invention, an electric conductivity measurement unit measures electric conductivity in the liquid and the current/density converter unit converts to produce the density of specific material in the specimen in proportion to the electric conductivity measured. This compensates for any effect on the reaction (oxidation/reduction capability) due to difference in electric conductivity of the liquid (i.e. difference in ion density and amount of active species). Therefore, the present invention provides higher precision for measurement.

In addition, in the polarographic densitometer according to the present invention, an immersion measurement unit determines that the sensor unit is immersed in the liquid in the standby interval and an impedance reduction circuit switching unit switches the impedance reduction circuit to no-connection mode for a period during which determination is done by said immersion measurement unit within the standby interval. Accordingly, there is no electric current passed between the electrodes due to the fact that the impedance reduction circuit enters no-connection mode in the standby interval. As the result, the electrodes have no chemical reaction, which can prolong the service life of the electrodes.

Moreover, in the polarographic densitometer according to the present invention, a working electrode switching unit is provided for switching the connection of the plurality of working electrodes in such order that the working electrode having the smallest area is initially connected. In particular, the working electrode having smaller area for providing higher reaction speed than that having larger area is initially put into operation, but up to some intermediate point in the reaction process, and thereafter, another working electrode having larger area is substituted for. This is advantageous in that further reduction in measurement time is attained.

Furthermore, in the polarographic densitometer according to the present invention, an offset current calibration unit calibrates any offset current that may be caused when the specified voltage is applied by said voltage applying circuit, a current amplifier circuit amplifies the current output from the sensor, and an amplifying factor control unit controls the amplifying factor for the current from said current amplifier circuit. As the result, highly precise specified voltage is applied to the sensor unit to produce any reaction precisely in proportion to the density of specific material in the specimen (liquid or gas) and to allow current amplification for any of reactions. Advantageously, this provides higher precision and wider range for measurement.

Finally, in the polarographic densitometer according to the present invention, a specified voltage controller unit provides variable control to produce such specified voltage from said voltage applying circuit that causes reaction of said group of electrodes in the specimen in proportion to the density of specific material selected by a selection unit. This allows for measurement of the density of a plurality of specific materials in the specimen. Accordingly, the present invention can provide wider application and higher usefulness.

BRIEF DESCRIPTION OF THE DRAWINGS

Now, embodiments of the present invention will be described in more detail with reference to the accompanying drawings, in which.

BEST FORM FOR EMBODYING THE INVENTION

A polarographic densitometer according to the present invention consists of a voltage applying circuit, a sensor unit, an impedance reduction circuit and a current/density conversion unit.

The voltage applying circuit applies specified voltage by which the sensor unit becomes responsive to the density of specific material in specimen (liquid or gas).

The sensor unit includes a group of electrodes to produce a current output in response to any reaction caused in the specimen when the specified voltage is applied by said voltage applying circuit.

The impedance reduction circuit reduces impedance of the specimen between said electrodes of the group.

The current/density conversion unit converts the current output of said sensor unit when the impedance is reduced by said impedance reduction circuit into the density of specific material in the specimen.

The polarographic densitometer configured as described above is operated in such manner that, when the voltage applying circuit applies specified voltage by which the sensor unit becomes responsive to the density of specific material in specimen, the sensor unit produces the current output due to any reaction in proportion to the density of specified material in the specimen, while reducing the impedance of the specimen by the impedance reduction circuit, and then, the current/density conversion unit converts the current output into the density of specific material in the specimen. Thus, measurement of the density of specific material is performed. More precisely, electric current flows through the impedance reduction circuit so that the impedance between the electrodes is reduced, making the reaction more stable. As the result, the polarographic densitometer according to the present invention is advantageous in that the linearity and repeatability is enhanced and the time period for measurement is shortened.

Figure 13A:
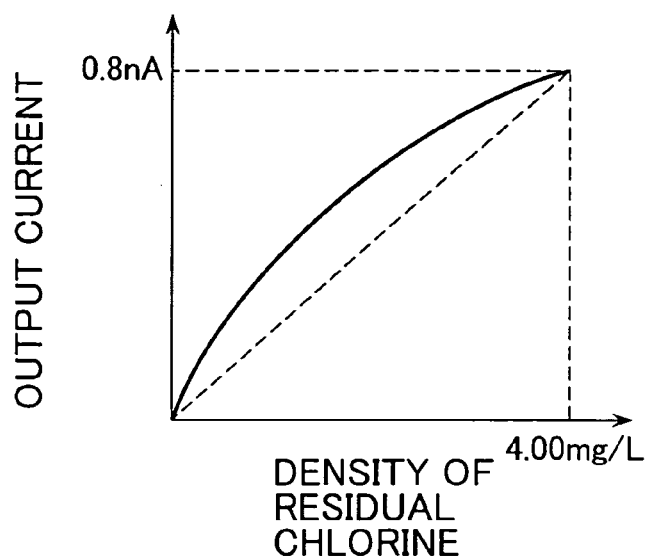
FIGS. 13A, 13B and 13C are graphs each illustrating any effect on performance (Linearity) of the device.
Figure 13B:
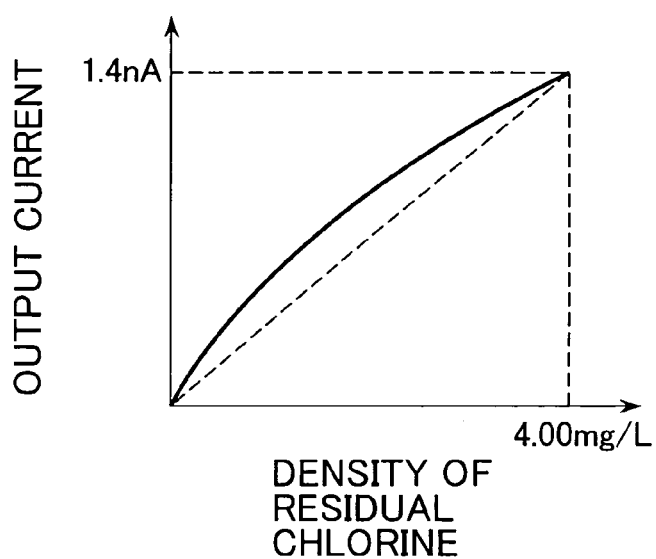
Figure 13C:
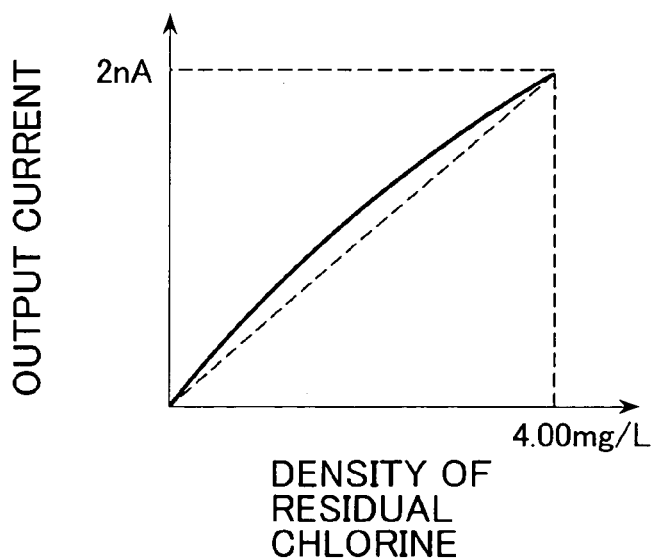

Now, brief description is made to enhancement in linearity with reference to FIGS. 13A to 13C. In particular, FIG. 13A illustrates the result of measurement by plotting the current output of the sensor unit when the impedance reduction circuit is in no-connection mode on the ordinate and the density of specific material (e.g. the density of residual chlorine) converted by the current/density conversion unit on the abscissa. FIGS. 13B and 13C illustrate the measurement results in the same condition as FIG. 13A, except that the impedance reduction circuit is in connection mode. It is noted that difference between FIGS. 13A and 13B is that the impedance reduction circuit has different load constant. As can be seen in those figures, the linearity becomes enhanced when the impedance reduction circuit is in connection mode. It also becomes enhanced with increase in load constant (i.e. resistance value) in the impedance reduction circuit.

Figure 16A:
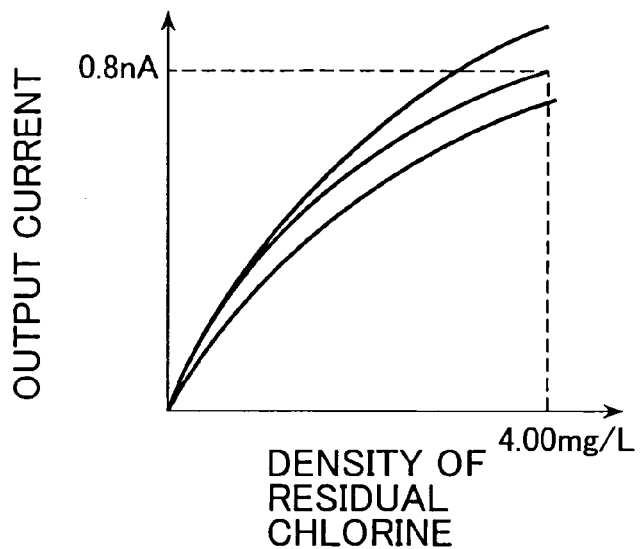
FIGS. 16A to 16C are graphs each illustrating any effect on performance (repeatability) of the device.
Figure 16B:
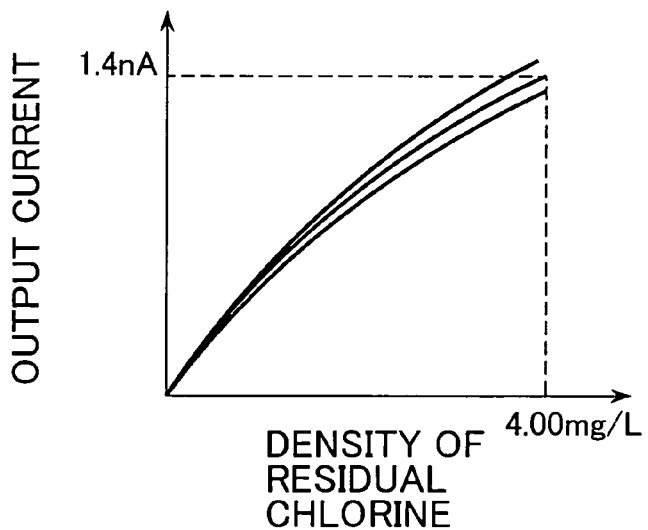
Figure 16C:
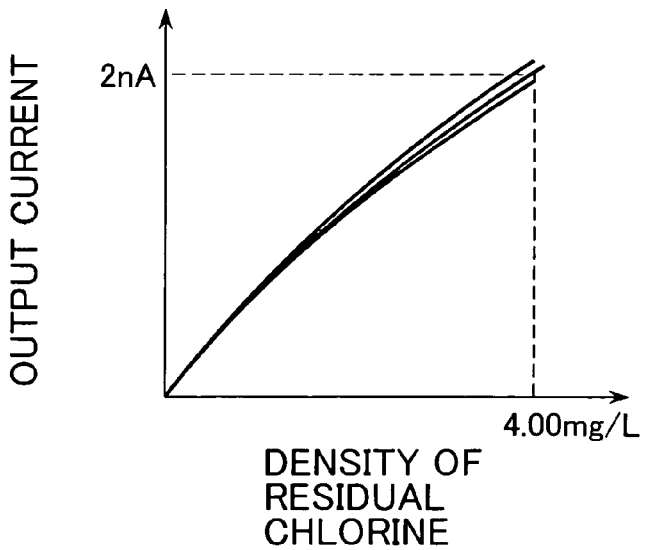

Then, brief description is made to enhancement in repeatability with reference to FIGS. 16A to 16C. In particular, FIG. 16A illustrates the result of measurements repeated plural times by plotting the current output of the sensor unit when the impedance reduction circuit is in no-connection mode on the ordinate and the density of specific material (e.g. the density of residual chlorine) converted by the current/density conversion unit on the abscissa. FIGS. 16B and 16C illustrate the measurement results in the same condition as FIG. 16A, except that the impedance reduction circuit is in connection mode. It is noted that difference between FIGS. 16A and 16B is that the impedance reduction circuit has different load constant. As can be seen in those figures, the repeatability becomes enhanced when the impedance reduction circuit is in connection mode. It also becomes enhanced with increase in load constant (i.e. resistance value) in the impedance reduction circuit.

Figure 17A:
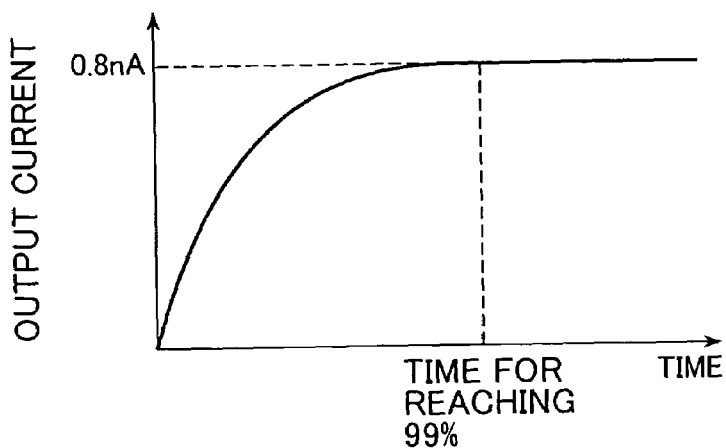
FIGS. 17A to 17C are graphs each illustrating any effect on performance (measurement time) of the device.
Figure 17B:
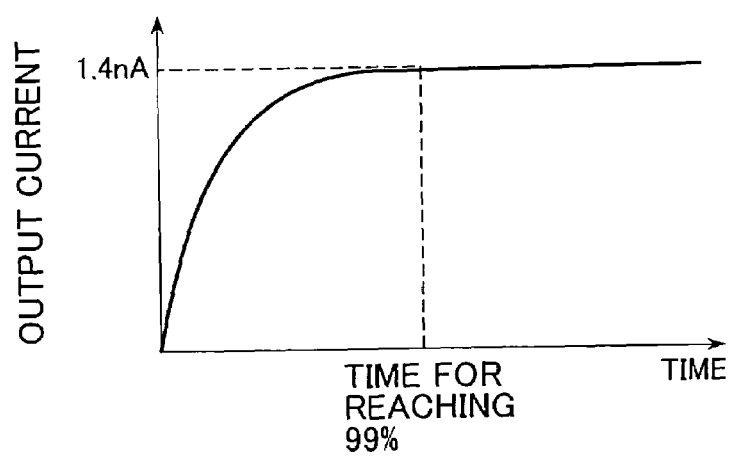
Figure 17C:
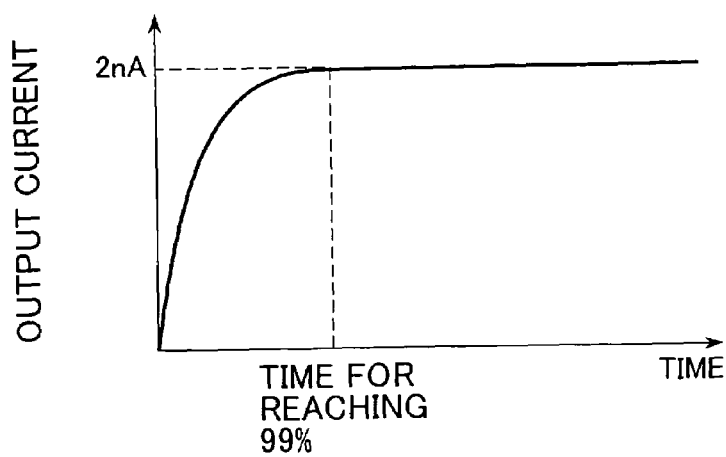

Next, brief description is made to shortening in measurement time with reference to FIGS. 17A to 17C. In particular, FIG. 17A illustrates the result of measurement by plotting the current output of the sensor unit when the impedance reduction circuit is in no-connection mode on the ordinate and the measurement time on the abscissa. FIGS. 17B and 17C illustrate the measurement results in the same condition as FIG. 17A, except that the impedance reduction circuit is in connection mode. It is noted that difference between FIGS. 17A and 17B is that the impedance reduction circuit has different load constant. As can be seen in those figures, shortening in measurement time becomes enhanced when the impedance reduction circuit is in connection mode. It also becomes enhanced with increase in load constant (i.e. resistance value) in the impedance reduction circuit.

The polarographic densitometer configured in such manner will be described in more detail in "Embodiment 1".

If the specimen is liquid, the densitometer of the present invention may further comprise an electric conductivity measurement unit for measuring the electric conductivity of the liquid between any of electrodes of the electrode group, and the current/density conversion unit may convert the current output of said sensor unit in proportion to the electric conductivity measured by said electric conductivity measurement unit into the density of specific material in the liquid specimen.

In the polarographic densitometer configured in such manner, the electric conductivity measurement unit may measure electric conductivity in the liquid and the current/density converter unit may convert the current output of the sensor unit into the density of specific material in the specimen in proportion to the electric conductivity thus measured. This can produce the density of specific material in proportion to the electric conductivity of the liquid. Accordingly, the present invention compensates for any effect on the reaction (oxidation/reduction capability) due to difference in electric conductivity of the liquid (i.e. difference in ion density and amount of active species), thereby providing higher precision for measurement.

Figure 18:
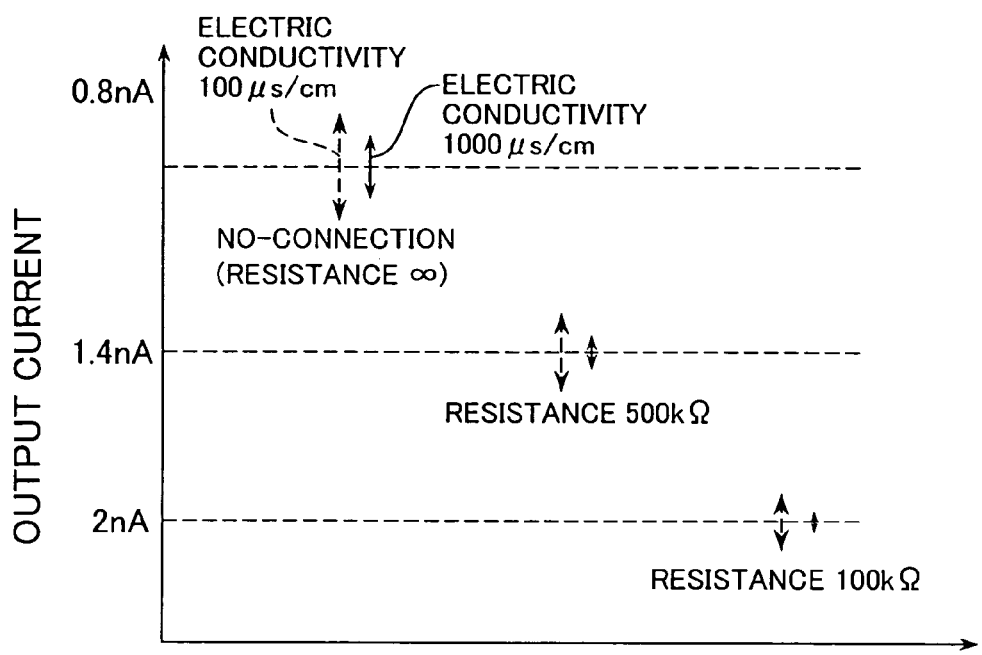
FIG. 18 is a graph illustrating any effect due to electric conductivity.

Then, brief description is made to providing higher precision with reference to FIG. 18. In particular, FIG. 18 illustrates the result of measurement by plotting the current output of the sensor unit on the ordinate and the load constant (resistance value) of the impedance reduction circuit on the abscissa. As can be seen in the figure, any irregularity in measurement result becomes smaller when the impedance reduction circuit is in connection mode. It also becomes smaller with increase in load constant (i.e. resistance value) in the impedance reduction circuit.

The oxidation/reduction potentiometer configured in such manner will be described in more detail in "Embodiment 3".

If the specimen is liquid, the densitometer of the present invention may further comprise: an immersion measurement unit; and an impedance reduction circuit switching unit, wherein the immersion measurement unit determines that the sensor unit is immersed in the liquid between any of the electrodes of the group within a standby interval before the current/density conversion unit starts to convert the current output into the density of specific material, and the impedance reduction circuit switching unit switches the impedance reduction circuit to no-connection mode for a period during which determination is done by said immersion measurement unit within the standby interval.

In the polarographic densitometer configured in such manner, the immersion measurement unit may determine that the sensor unit is immersed in the liquid in the standby interval and the impedance reduction circuit switching unit may switch the impedance reduction circuit to no-connection mode for a period during which determination is done by said immersion measurement unit within the standby interval. Accordingly, there is no electric current passed between the electrodes due to the fact that the impedance reduction circuit enters no-connection mode in the standby interval. As the result, the electrodes have no chemical reaction, which can prolong the service life of the electrodes.

Figure 19:
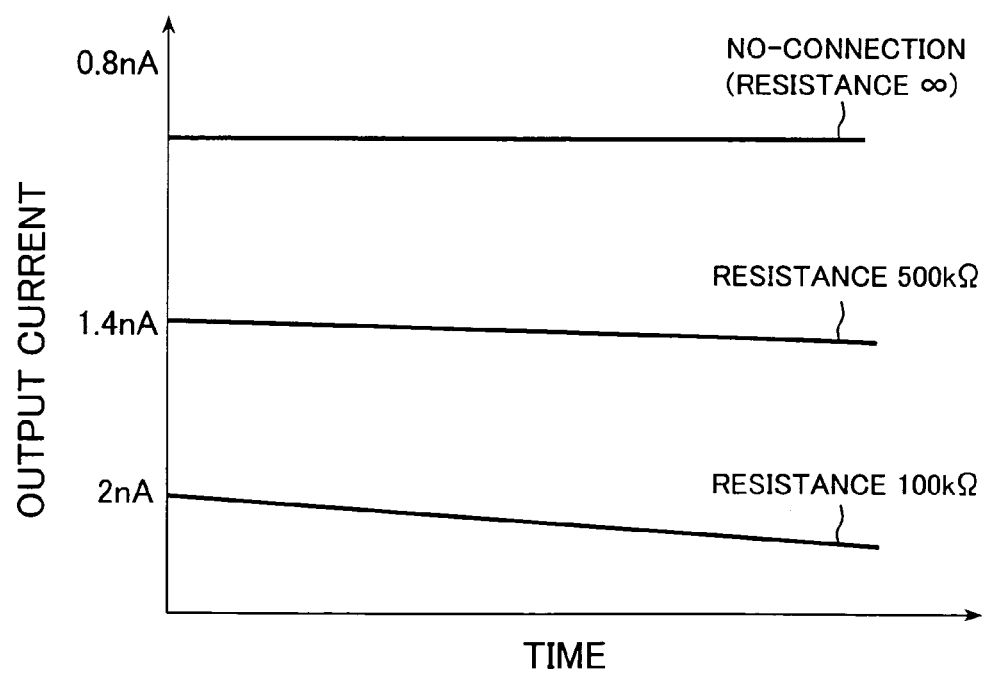
FIG. 19 is a graph illustrating any reduction in output due to immersion.

Then, brief description is made to providing extended service life of the electrodes with reference to FIG. 19. In particular, FIG. 19 illustrates the result of measurement by plotting the current output of the sensor unit on the ordinate and the time period during which the sensor unit is immersed in the liquid on the abscissa. As can be seen in the figure, when the impedance reduction circuit is in connection mode any deterioration of the electrodes due to reaction has been occurred with increase in time period during which the sensor unit is immersed. On the other hand, when the impedance reduction circuit is in no-connection mode the service life of the electrodes can be prolonged.

The polarographic densitometer configured in such manner will be described in more detail in "Embodiment 4".

In the polarographic densitometer of the present invention the group of electrodes may consist of a counter/reference electrode to which the specified voltage is applied by the voltage applying circuit and a plurality of working electrodes each having different area to produce the current in response to any reaction caused in the specimen in conjunction with said counter/reference electrode, the impedance reduction circuit may reduce the impedance of the specimen between said counter/reference electrode and each of said working electrodes, and a working electrode switching unit may be provided for switching the connection of the plurality of working electrodes in such order that the working electrode having the smallest area is initially connected. Alternatively, the group of electrodes may consist of a reference electrode by which a reference voltage is developed in the specimen for providing the specified voltage output from the voltage applying circuit, a counter electrode to which the specified voltage output from the voltage applying circuit is applied, and a plurality of working electrodes each having different area to produce the current in response to any reaction caused in the specimen in conjunction with said counter/reference electrode, the impedance reduction circuit may reduce the impedance of the specimen between the counter electrode and each of the working electrodes, and a working electrode switching unit may be provided for switching the connection of the plurality of working electrodes in such order that the working electrode having the smallest area is initially connected.

In the polarographic densitometer configured in such manner, the working electrode switching unit may switch the connection of the plurality of working electrodes in such order that the working electrode having the smallest area is initially connected. In particular, the working electrode having smaller area for providing higher reaction speed than that having larger area is initially put into operation, but up to some intermediate point in the reaction process, and thereafter, another working electrode having larger area is substituted for. Advantageously, further reduction in measurement time can be attained.

Figure 20:
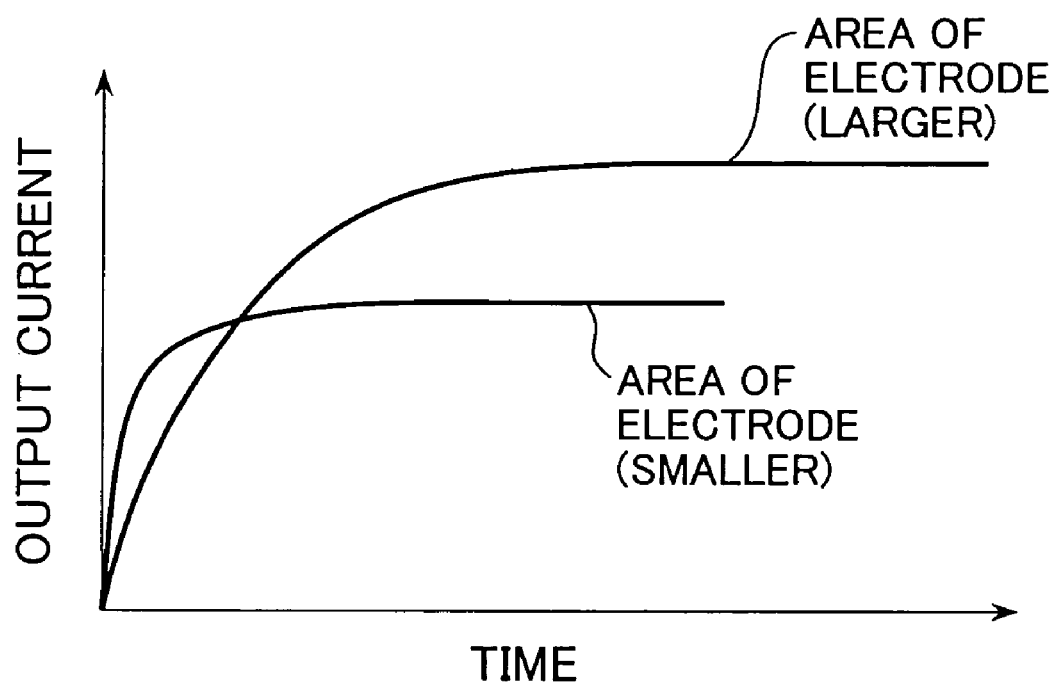
FIG. 20 is a graph illustrating any effect due to area of an electrode.

Then, brief description is made to reduction in measurement time with reference to FIG. 20. In particular, FIG. 20 illustrates the result of measurement by plotting the current output of the sensor unit on the ordinate and the reaction time on the abscissa. As can be seen in the figure, the reaction time until substantially saturated condition reaches is shorter for the electrode having smaller area than that having larger area, and therefore, the measurement time can be shortened if the electrode having smaller area is used for measurement in some part of the whole reaction process.

The polarographic densitometer configured in such manner will be described in more detail in "Embodiment 5".

The polarographic densitometer of the present invention may further comprise an offset current calibration unit for calibrating any offset current that may be caused when the specified voltage is applied by said voltage applying circuit. In addition, the densitometer may further comprise a current amplifier circuit for amplifying the current output from the sensor when the impedance is reduced by said impedance reduction circuit, and an amplifying factor control unit for controlling the amplifying factor for the current amplifier circuit.

In the polarographic densitometer configured in such manner, the offset current calibration unit calibrates any offset current that may be caused when the specified voltage is applied by said voltage applying circuit, the current amplifier circuit amplifies the current output from the sensor, and the amplifying factor control unit controls the amplifying factor for the current amplifier circuit. As the result, highly precise specified voltage is applied to the sensor unit to precisely produce any reaction in proportion to the density of specific material in the specimen (liquid or gas) and to allow current amplification for various reactions. Advantageously, this can provide higher precision and wider range for measurement.

The polarographic densitometer configured in such manner will be described in more de tail in "Embodiment 2".

Figure 1:
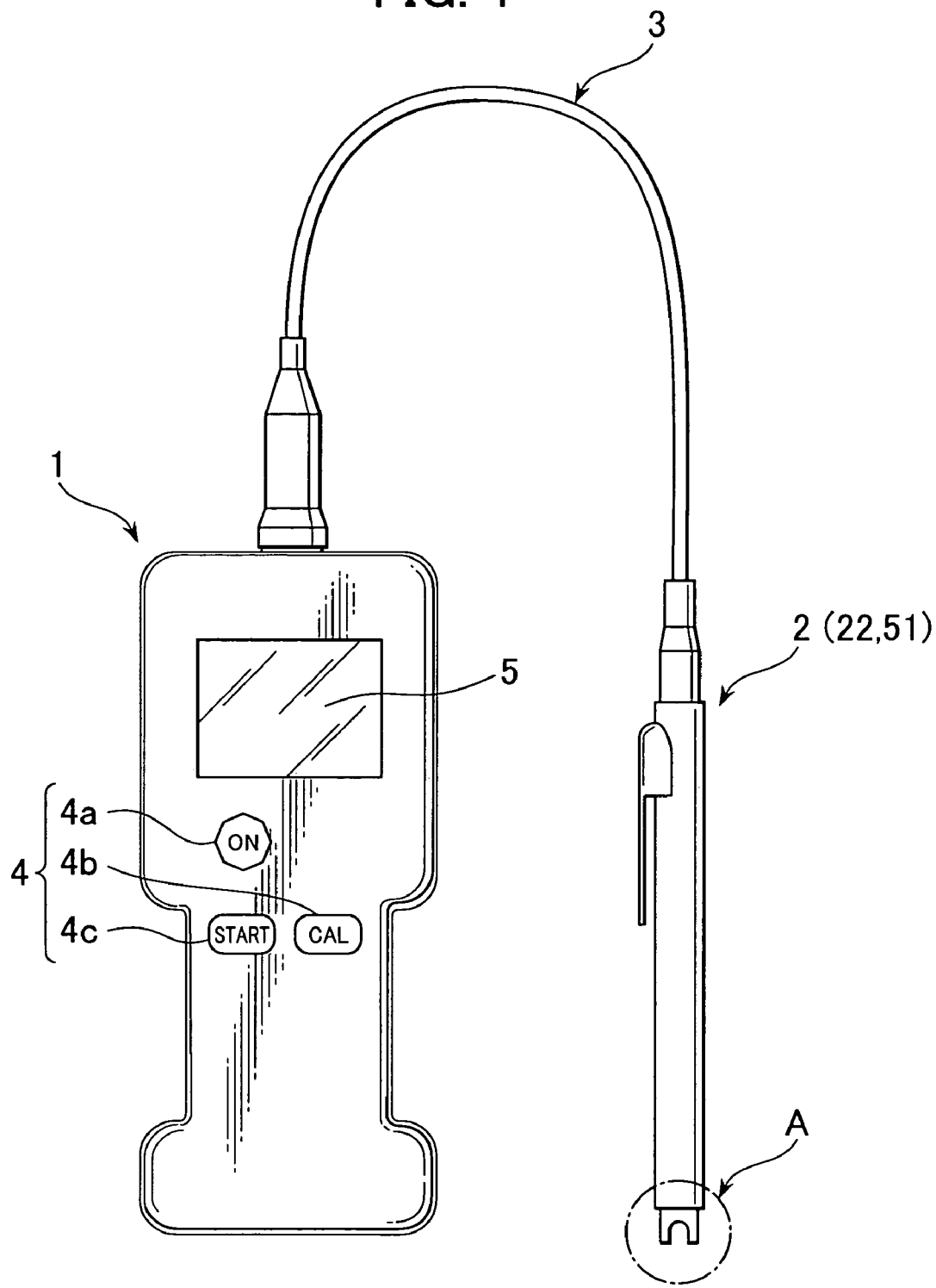
FIG. 1 is an external view illustrating a polarographic densitometer according to the present invention (Embodiments 1, 2, 3, 4 and 5)
Figure 2:
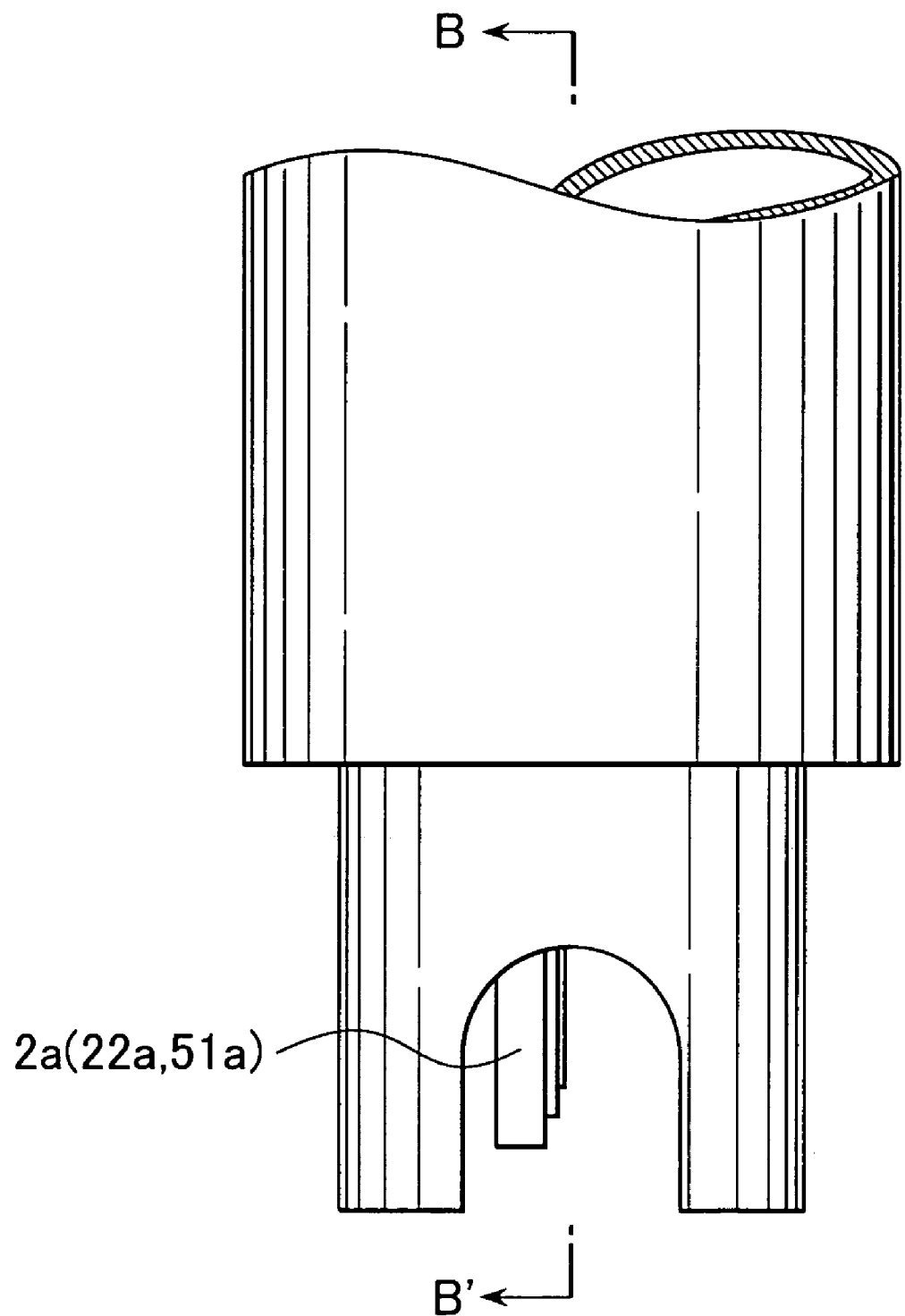
FIG. 2 is an enlarged view illustrating a detector portion of a sensor unit of the densitometer (Embodiments 1, 2, 3, 4 and 5)
Figure 3:
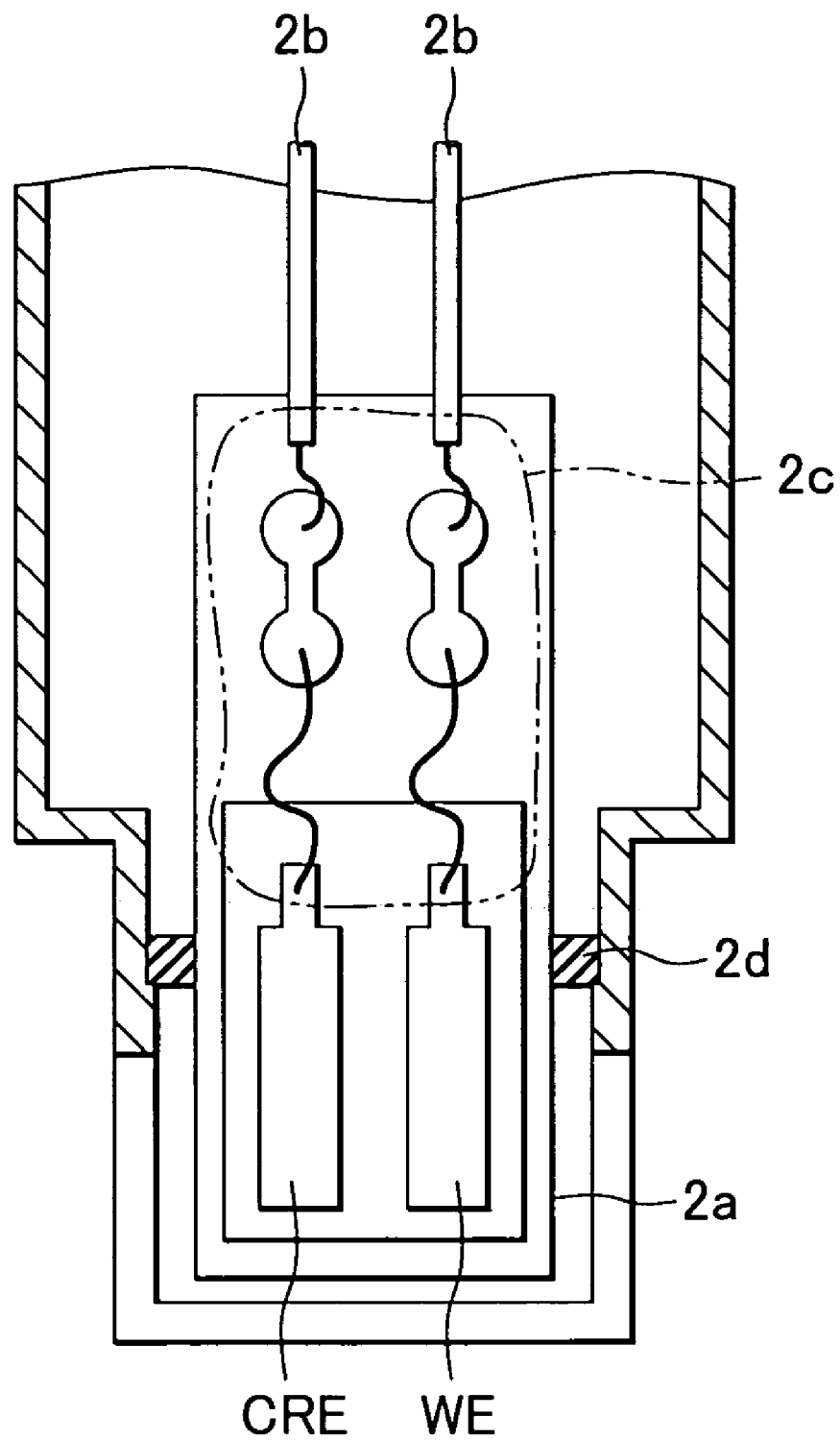
FIG. 3 is a cross-section view taken along a line B–B' in FIG. 2, illustrating an internal portion of the detector (Embodiment 1)
Figure 4:
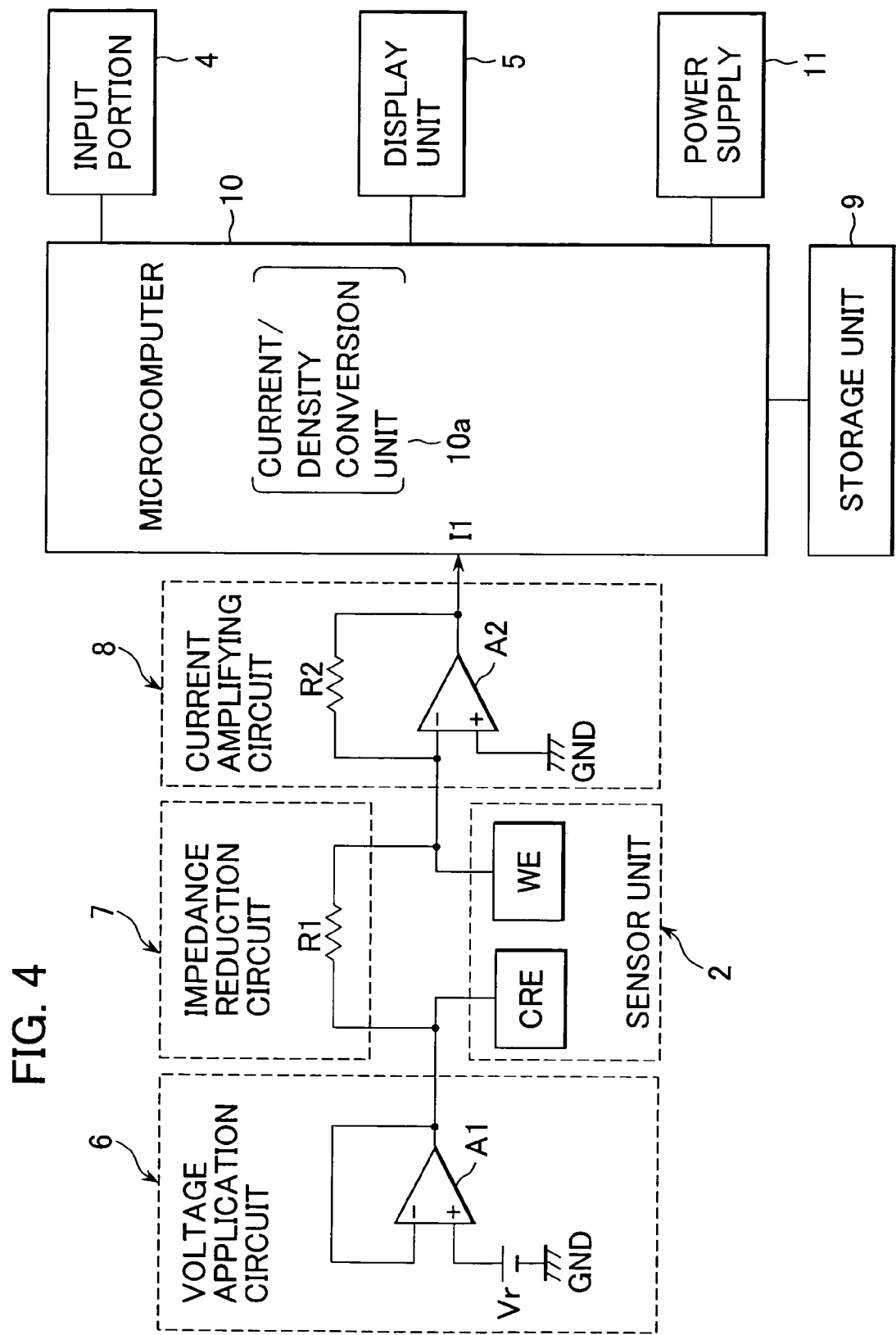
FIG. 4 is a block diagram of the polarographic densitometer (Embodiment 1)

Embodiment 1:

A polarographic densitometer according to Embodiment 1 of the present invention will be described with reference to the drawings: FIG. 1 that is an external view of the densitometer; FIG. 2 that is an enlarged view of a detector portion; FIG. 3 that is an internal view of the detector portion; and FIG. 4 that is a block diagram of the densitometer.

The polarographic densitometer of the embodiment comprises a body portion 1 having an input portion 4 (4*a*, 4*b* & 4*c*) and a display unit 5 both provided on the front side thereof, a sensor unit 2 having a group of electrodes (a counter/reference electrode "CRE" and a working electrode "WE") mounted therein, and a cable 3 for connecting between the body portion 1 and the sensor unit 2. The body portion 1 includes a voltage applying circuit 6, an impedance reduction circuit 7, a current amplifying circuit 8, a storage unit 9 and a microcomputer 10, all mounted on an electronic board. In addition, a power supply 11 is included in the body portion 1.

The input portion 4 includes an "ON" key 4*a*, a "START" key 4*b* and a "CAL" key 4, which are used for power up, start for measurement, and calibration for the device, respectively. In particular, the "ON" key 4*a* acts to supply electric power from the power supply 11 to various components of the electrical system in the device. The "START" key 4*b* is provided for starting measurement, and the "CAL" key 4*c* acts to enter the device into calibration mode.

The display unit 5 is made up of an "LCD" and displays input condition, measurement result, calibration mode, remaining battery capacity, etc.

The sensor unit 2 includes, within an end portion (i.e. a detector portion) "A" of a rod member, a board 2*a* on which a counter/reference electrode (e.g. silver chloride) "CRE" and a working electrode (e.g. platinum) "WE" are mounted. In addition, electric wires 2*b* extend from the electrodes through the inner portion of the rod member to the electronic board in the body portion. Connection between the electric wires 2*b* and the board 2*a* is covered with a water-proof and protective coating 2*c*. Furthermore, a packing 2*d* is provided for preventing any specimen (in this embodiment, liquid) from entering inside of the rod member.

The power supply 11 feeds electric power to each of various components of the electrical system.

The voltage applying circuit 6 consists of a voltage follower to which a basic voltage "Vr" for the group of electrodes (the counter/reference electrode "CRE" and the working electrode "WE") to only react with specific material (in this embodiment, chlorine) of the specimen (in this embodiment, liquid) is input and from which the specified voltage is output.

The impedance reduction circuit 7 consists of a resistor "R1" connected between the counter/reference electrode "CRE" and the working electrode "WE" in order to reduce any impedance created between the counter/reference electrode "CRE" and the working electrode "WE" when they are immersed in the liquid.

The current amplifying circuit 8 consists of a well known reversed type amplifier circuit for amplifying the current output which is fed from the sensor unit 2 but reduced in amplitude by the impedance reduction circuit 7.

The storage unit 9 consists of an "EEPROM" in which various types of data are stored.

The microcomputer 10 has a current/density conversion unit 10*a* incorporated therein and performs various types of operation such as conversion of analogue data acquired into digital data, calculation of density of specific material and other types of data, etc. The current/density conversion unit 10*a* converts the current from the current amplifying circuit 8 into the density of chlorine in the liquid.

Now, operation of the polarographic densitometer configured according to Embodiment 1 will be described in more detail.

When the "ON" key 4*a* on the device is depressed an electric power is fed from the power supply 11 to each of various components of the electrical system, and then, the device enters the standby mode. Thereafter, depressing the "START" key 4*b* makes the measurement operation started. In particular, when the "START" key 4*b* is depressed the specified voltage is output from the voltage follower. Then, when the end portion (i.e. the detector portion) "A" of the sensor unit 2 is immersed in the liquid it enters inside of the end portion "A" so that the group of electrodes (the counter/reference electrode "CRE" and the working electrode "WE") are immersed in the liquid. An electric current is produced to flow between the electrodes (the counter/reference electrode "CRE" and the working electrode "WE") in proportion to the density of specific material (in this embodiment, chlorine) in the liquid. Certain electric current also flows through the resistor "R1" between the counter/reference electrode "CRE" and the working electrode "WE".

Then, the electric current produced is amplified in the current amplifying circuit 8 and is fed to the microcomputer 10 for conversion into digital current signal. Thereafter, the current/density conversion unit 10*a* converts the digital current signal into the density of chlorine, which is displayed on the display unit 5.

Now, any effect on the performance (e.g. linearity and repeatability) of the device due to the resistor "R1" connected between the counter/reference electrode "CRE" and the working electrode "WE" will be described with reference to FIGS. 14A to 14F.

Figure 14A:
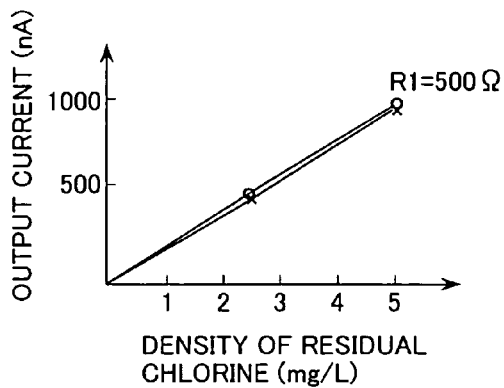
FIGS. 14A to 14F are graphs each illustrating any effect on performance (linearity and repeatability) of the device due to an impedance reduction circuit i.e. a resistor) (Embodiment 1)
Figure 14D:
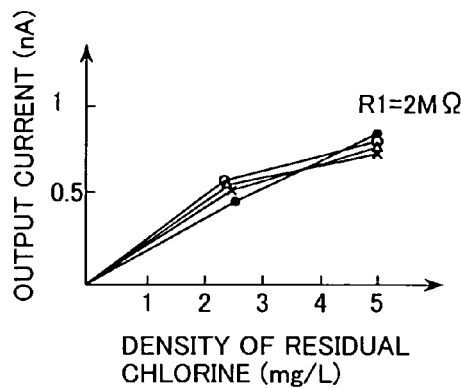
Figure 14B:
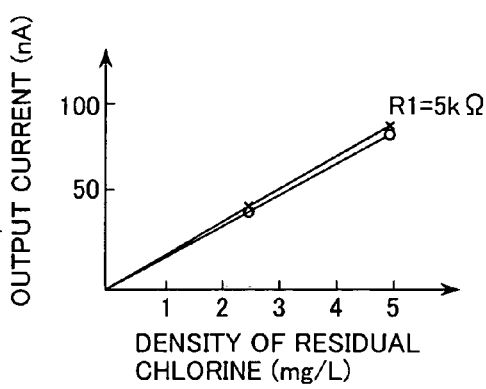
Figure 14E:
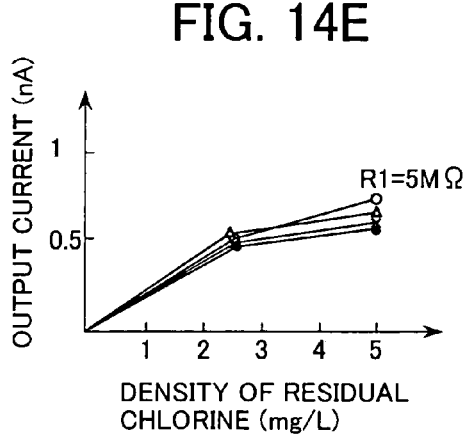
Figure 14C:
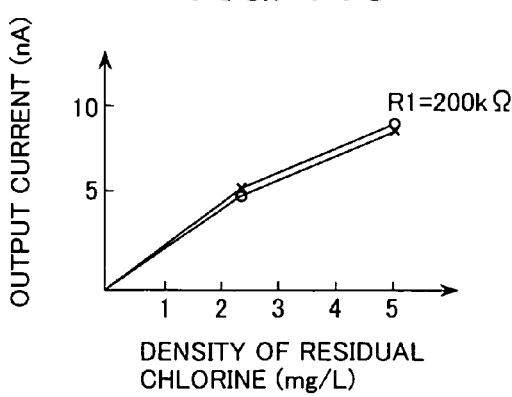
Figure 14F:
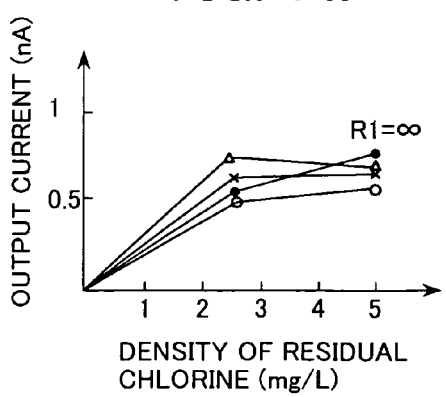

FIGS. 14A to 14F are graphs each illustrating the relation between the current output from the sensor unit 2 plotted on the ordinate and the density of residual chlorine plotted on the abscissa. FIGS. 14A to 14F illustrate the results of measurement in such condition that the resistor "R1" has resistance of 500Ω, 5 kΩ, 200 kΩ, 2 MΩ, 5 MΩ, and ∞, respectively. If the resistor "R1" is connected between the counter/reference electrode "CRE" and the working electrode "WE" (FIGS. 14A to 14E), substantially higher performance of linearity and repeatability can be attained than the case where no such resistor "R1" is connected therebetween (FIG. 14F).

Figure 5:
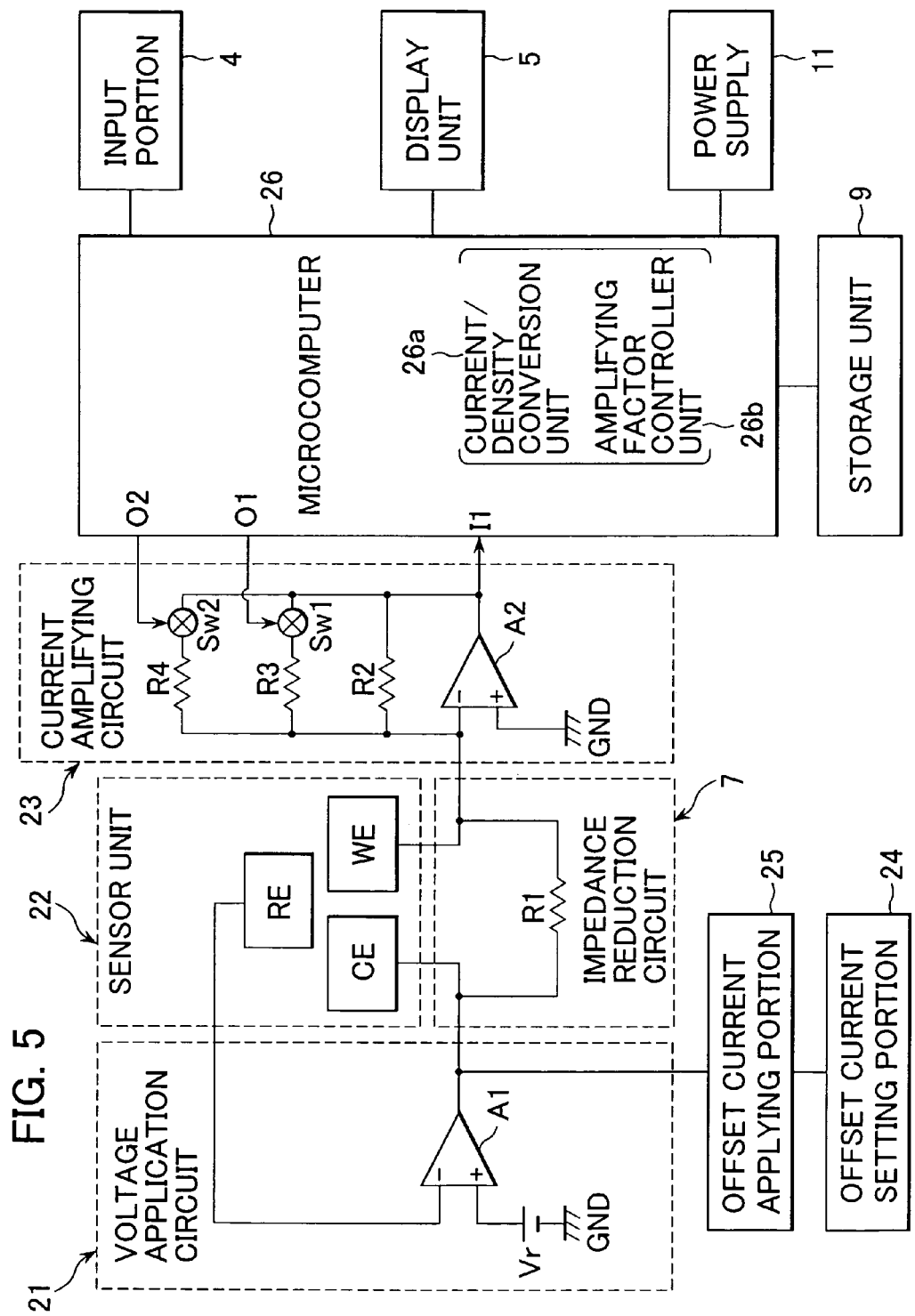
FIG. 5 is a block diagram of the polarographic densitometer (Embodiment 2)

Embodiment 2:

A polarographic densitometer according to Embodiment 2 of the present invention will be described with reference to the drawings: FIG. 1 that is an external view of the densitometer; FIG. 2 that is an enlarged view of a detector portion; FIG. 5 that a block diagram; and FIG. 6 that is an internal view of the detector portion.

The polarographic densitometer of this embodiment comprises a body portion 1 having an input portion 4 (4a, 4b & 4c) and a display unit 5 both provided on the front side thereof, a sensor unit 22 having a group of electrodes (a reference electrode "RE", a counter electrode "CE" and a working electrode "WE") mounted therein, and a cable 3 for connecting between the body portion 1 and the sensor unit 22. The body portion 1 includes a voltage applying circuit 21, an offset current setting portion 24, an offset current applying portion 25, an impedance reduction circuit 7, a current amplifying circuit 23, a storage unit 9 and a microcomputer 26, all mounted on an electronic board. In addition, a power supply 11 is included in the body portion 1. The offset current setting portion 24 and the offset current applying portion 25 form an offset current calibration unit.

The input portion 4 includes an "ON" key 4a, a "START" key 4b and a "CAL" key 4, which are used for power up, start for measurement, and calibration for the device, respectively. In particular, the "ON" key 4a acts to supply electric power from the power supply 11 to various components of the electrical system in the device. The "START" key 4b is provided for starting measurement, and the "CAL" key 4c acts to enter the device into calibration mode.

The display unit 5 is made up of an "LCD" and displays input condition, measurement result, calibration mode, remaining battery capacity, etc.

The sensor unit 22 includes, within an end portion (i.e. a detector portion) "A" of a rod member, a board 22a on which a reference electrode (e.g. silver chloride) "RE", a counter electrode (e.g. platinum) "CE" and a working electrode (e.g. platinum) "W" are mounted. In addition, electric wires 22b extend from the electrodes through the inner portion of the rod member to the electronic board in the body portion 1. Connection between the electric wires 22b and the board 22a is covered with a water-proof and protective coating 22c. Furthermore, a packing 22d is provided for preventing any specimen (in this embodiment, liquid) from entering inside of the rod member.

The power supply 11 feeds electric power to each of various components of the electrical system.

The voltage applying circuit 21 consists of a potentiostat to which a basic voltage "Vr" for the group of electrodes (the reference electrode "RE", the counter electrode "CE" and the working electrode "WE") to only react with specific material (in this embodiment, chlorine) of the specimen (in this embodiment, liquid) and a reference voltage developed in the specimen are input, and from which the specified voltage is output.

The offset current setting portion 24 consists of a dip switch that is used to set the level of electric current for canceling any offset current that may be caused when the specified voltage is output from the potentiostat.

The offset current applying portion 25 produces electric current at the level set by the offset current setting portion 24 for canceling any offset current and applies it to the output of the potentiostat.

The impedance reduction circuit 7 consists of a resistor "R1" connected between the counter electrode "CE" and the working electrode "WE" in order to reduce any impedance created between the counter electrode "CE" and the working electrode "WE" when they are immersed in the liquid.

The current amplifying circuit 23 includes a well known reversed type amplifier circuit having feedback resistors "R3", "R4" and switches "Sw1", "Sw2" connected as shown. The current amplifying circuit 23 amplifies the current output which is fed from the sensor unit 22 but reduced in amplitude by the impedance reduction circuit 7 by operating any of switches "Sw1", "Sw2" depending on the amplifying factor controlled by an amplifying factor controller unit 26b, as described later.

The storage unit 9 consists of an "EEPROM" in which various types of data are stored.

The microcomputer 26 has a current/density conversion unit 26a and an amplifying factor controller unit 26b incorporated therein and performs various types of operation such as conversion of analogue data acquired into digital data, calculation of density of specific material and other types of data, etc. The current/density conversion unit 26a converts the current from the current amplifying circuit 23 into the density of chlorine in the liquid. The amplifying factor controller unit 26b controls to connect or disconnect the feedback resistors "R3" and "R4" by operation of the switches "Sw1" and "Sw2" in the current amplifying circuit 23.

Now, operation of the polarographic densitometer configured according to Embodiment 2 will be described in more detail.

When the "ON" key 4a on the device is depressed an electric power is fed from the power supply 11 to each of various components of the electrical system, and then, the device enters the standby mode. Thereafter, depressing the "START" key 4b makes the measurement operation started. In particular, when the "START" key 4b is depressed the offset current applying portion 25 supplies electric current at the level set by the offset current setting portion 24 for canceling any offset current, and the potentiostat outputs the specified voltage. Then, when the end portion i.e. the detector portion) "A" of the sensor unit 22 is immersed in the liquid it enters inside of the end portion "A" so that the group of electrodes (the reference electrode "RE", the counter electrode "CE" and the working electrode "WE") are immersed in the liquid. The reference voltage of the potentiostat is applied to the reference electrode "RE", and an electric current is produced to flow between the counter electrode "CE" and the working electrode "WE" in proportion to the density of specific material (in this embodiment, chlorine) in the liquid. Certain electric current also flows through the resistor "R1" between the counter electrode "CE" and the working electrode "WE".

Then, by turning ON or OFF the switches "Sw1" and "Sw2" according to the control signal from ports "O2" and "O3" of the amplifying factor controller unit (i.e. the microcomputer), the electric current from the sensor unit 22 is amplified by the current amplifying circuit 23 with the suitable amplifying factor. The electric current is, then, fed to the microcomputer 26 for digital conversion. The current/density conversion unit 26a converts it into the density of chlorine, which is displayed on the display unit 5.

Any effect on the performance of the device due to the resistor "R1" connected between the counter electrode "CE" and the working electrode "WE" is considered same as one that has been described in Embodiment 1 with reference to FIGS. 14A to 14F. However, because of the fact that any offset current is calibrated to allow current amplification for wider range of reactions then the polarographic densitometer of Embodiment 2 actually has more excellent performance than that of Embodiment 1.

Figure 6:
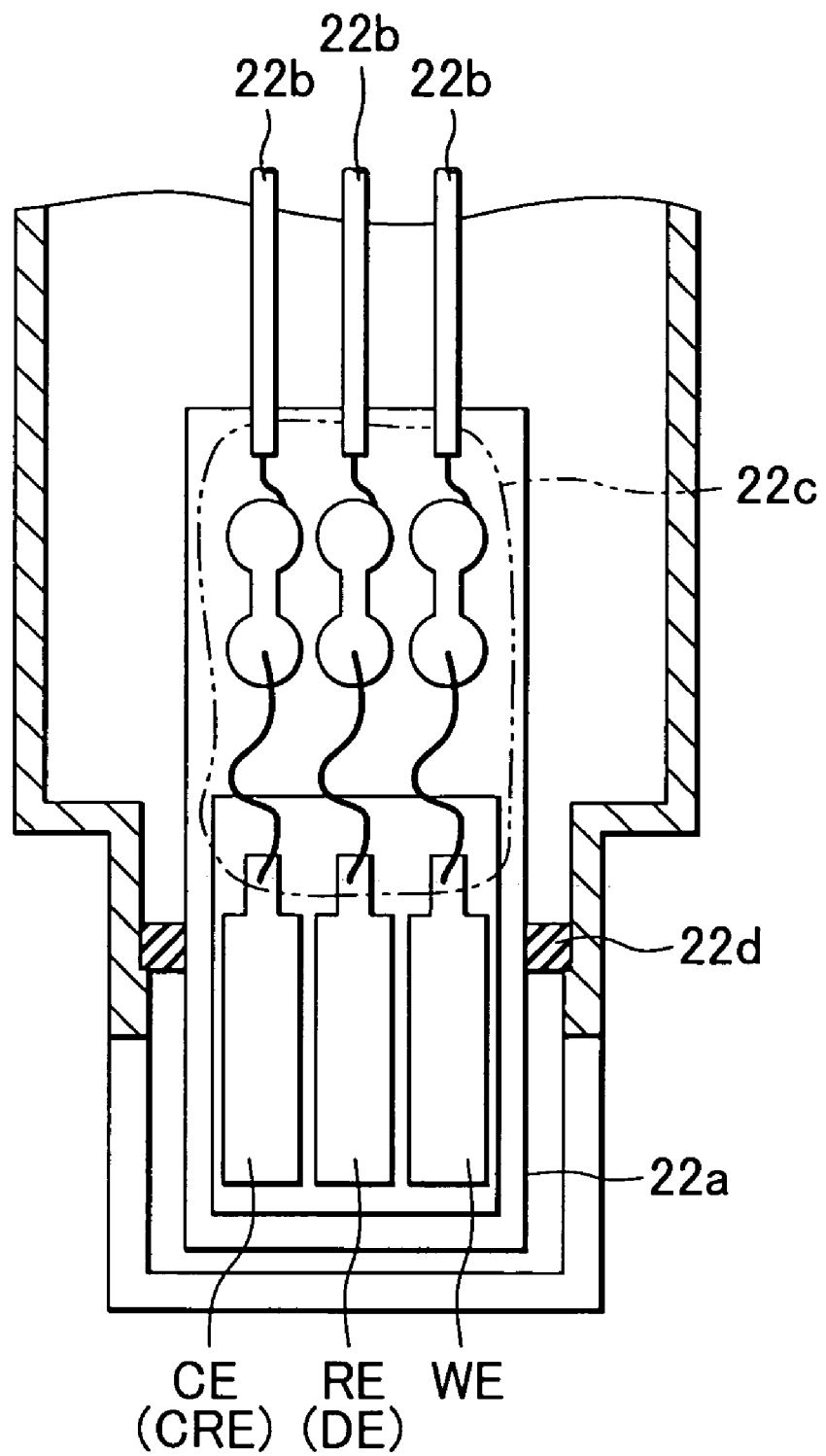
FIG. 6 is a cross-section view taken along a line B–B' in FIG. 2, illustrating an internal portion of the detector (Embodiments 2, 3 and 4)
Figure 7:
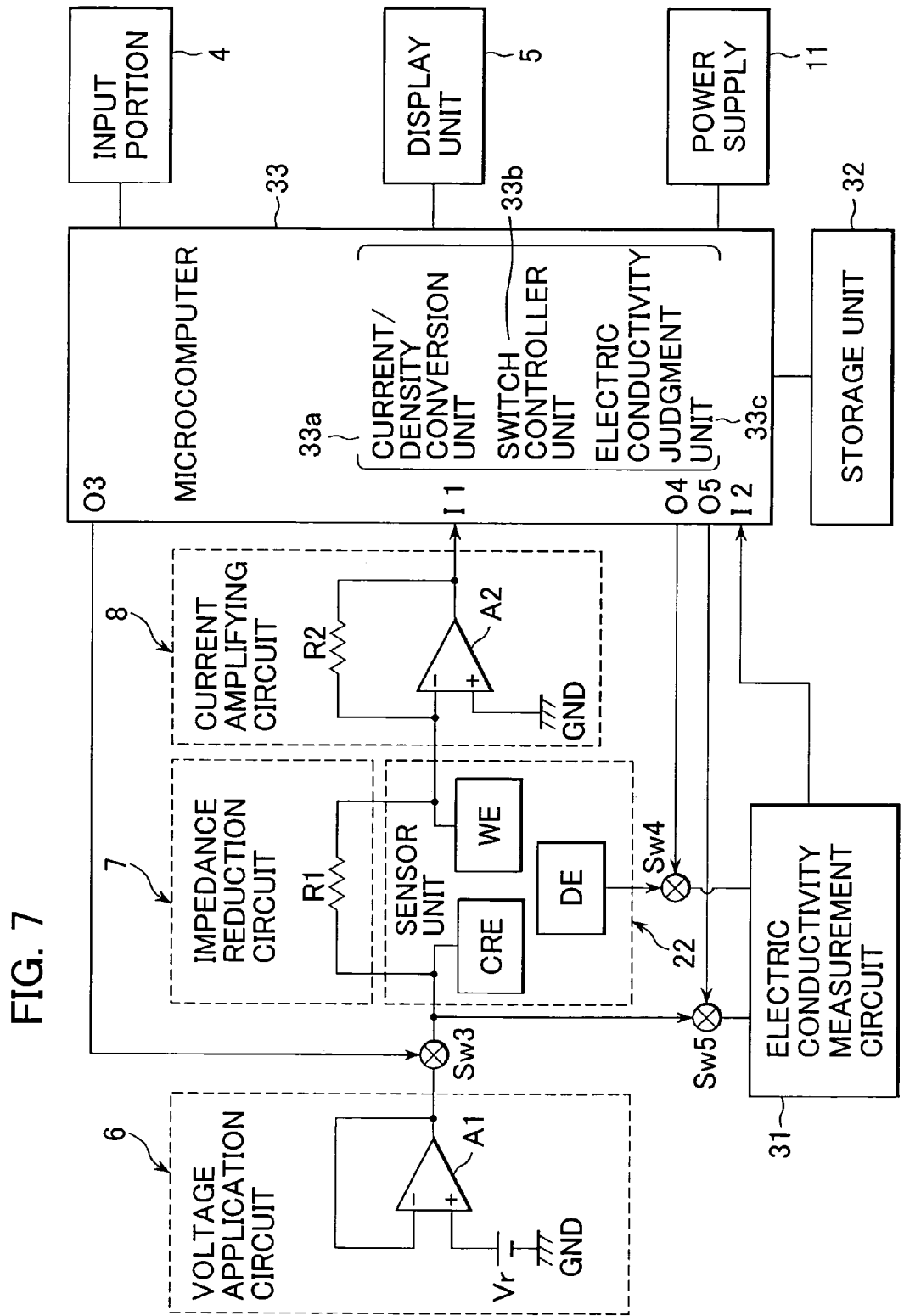
FIG. 7 is a block diagram of the polarographic densitometer (Embodiment 3)

Embodiment 3:

A polarographic densitometer according to Embodiment 3 of the present invention will be described with reference to the drawings: FIG. 1 that is an external view of the densitometer; FIG. 2 that is an enlarged view of a detector portion; FIG. 6 that is an internal view of the detector portion; and FIG. 7 that a block diagram of the densitometer.

The polarographic densitometer of this embodiment has an additional component or an electric conductivity measurement unit added to the configuration of Embodiment 1. Therefore, only the part or component of the polarographic densitometer that is different from that of Embodiment 1 will be described hereafter.

The electric conductivity measurement unit is made up of a dummy electrode "DE", an electric conductivity measurement circuit 31, switches "Sw3", "Sw4" & "Sw5", a switch controller unit 33b, a storage unit 32, and an electric conductivity judgment unit 33c, in order to measure electric conductivity of the liquid. The switch controller unit 33b and the electric conductivity judgment unit 33c are incorporated into a microcomputer 33, together with a current/density conversion unit 33a. A counter/reference electrode "CRE" and a working electrode "WE" added to the dummy electrode "DE" form a sensor unit 22.

The dummy electrode "DE" is used for detection of a voltage developed between it and the counter/reference electrode "CRE" in proportion to the electric conductivity of the liquid. The electric conductivity measurement circuit 31 amplifies the voltage developed between the dummy electrode "DE" and the counter/reference electrode "CRE". The switches "Sw3", "Sw4" & "Sw5" act to switch connection between the voltage applying circuit 6 or the electric conductivity measurement circuit 31 and the sensor unit 22. The switch controller unit 33b controls operation of the switches "Sw3", "Sw4" & "Sw5" so that either one of the voltage applying circuit 6 or the electric conductivity measurement circuit 31 is connected to the sensor unit 22. The storage unit 32 stores basic electrical conductivity that is judgment criterion for determining which class the electric conductivity of the liquid measured falls in. The storage unit 32 additionally stores correction factors set for each of the classes. The electric conductivity judgment unit 33c calculates the electric conductivity based on the voltage from the electric conductivity measurement circuit 31 and compares it with the basic electric conductivity stored in the storage unit 32. Then, it determines which class the electric conductivity of the liquid measured falls in and selects the correction factor corresponding to the class determined.

When the current/density conversion unit 33a converts the current from the current amplifying circuit 8 into the density of chlorine it performs correction depending on the correction factor selected by the electric conductivity judgment unit 33c.

Now, operation of the polarographic densitometer configured according to Embodiment 3 will be described in more detail.

When the "ON" key 4a on the device is depressed an electric power is fed from the power supply 11 to each of various components of the electrical system, and then, the device enters the standby mode. Thereafter, depressing the "START" key 4b makes the measurement operation started. In particular, when the "START" key 4b is depressed the specified voltage is output from the voltage follower. Then, when the end portion (i.e. the detector portion) "A" of the sensor unit 2 is immersed in the liquid it enters inside of the end portion "A" so that the group of electrodes (the counter/reference electrode "CRE" and the working electrode "WE") and the dummy electrode "DE" are immersed in the liquid.

Then, the switch "Sw3" is turned OFF according to OFF control signal from the port "O3" of the switch controller unit 33b (i.e. the microcomputer 33) and the switches "Sw4" and "Sw5" are turned ON according to ON control signal from the ports "O4" and "O5" of the switch controller unit 33b i.e. the microcomputer 33). Therefore, the voltage applying circuit 6 enters no-connection mode, while the electric conductivity measurement circuit 31 enters connection mode.

Then, the electric conductivity measurement circuit 31 amplifies and digitizes the voltage developed between the dummy electrode "DE" and the counter/reference electrode "CRE". Next, the electric conductivity judgment unit 33c calculates the electric conductivity based on the digitized voltage and compares it with the basic electric conductivity stored in the storage unit 32, in order to determine whether the electric conductivity of the liquid measured falls in "large class" or "small class", on the basis of which the correction factor is selected.

Then, the switch "Sw3" is turned ON according to ON control signal from the port "O3" of the switch controller unit 33b (i.e. the microcomputer 33) and the switches "Sw4" and "Sw5" are turned OFF according to OFF control signal from the ports "O4" and "O5" of the switch controller unit 33b (i.e. the microcomputer 33). Therefore, the voltage applying circuit 6 enters connection mode, while the electric conductivity measurement circuit 31 enters no-connection mode. The electric current is produced to flow between the electrodes (the counter/reference electrode "CRE" and the working electrode "WE") in proportion to the density of specific material (in this embodiment, chlorine) in the liquid. Certain electric current also flows through the resistor "R1" between the counter/reference electrode "CRE" and the working electrode "WE".

Then, the electric current produced is amplified in the current amplifying circuit 8 and is fed to the microcomputer 33 for conversion into digital current signal. Thereafter, the current/density conversion unit 33a converts the digital current signal into the density of chlorine, which is then corrected according to the correction factor selected by the electric conductivity judgment unit 33c. The corrected density of chlorine is then displayed on the display unit 5.

In this embodiment the densitometer has such configuration that the voltage applying circuit 6 consists of the voltage follower to which the basic voltage "Vr" for the group of electrodes to only react with specific material of the liquid is input and from which the specified voltage is output, and the group of electrodes consists of the counter/reference electrode "CRE" to which the specified voltage is applied by the voltage follower and the working electrode for producing the current in response to any reaction caused in the specimen in conjunction with the counter/reference electrode "CRE". However, the densitometer may have another configuration, as described in Embodiment 2, in which the voltage applying circuit consists of the voltage follower to which the basic voltage for the group of electrodes to only react with specific material of the liquid is input and from which the specified voltage is output, and the group of electrodes consists of the reference electrode "RE" by which the reference voltage is developed in the specimen for providing the specified voltage output from the voltage applying circuit, the counter electrode "CE" to which the specified voltage output from said voltage follower is applied, and the working electrode "WE" for providing the current in response to any reaction caused in the specimen in conjunction with said counter electrode "CE".

Figure 8:
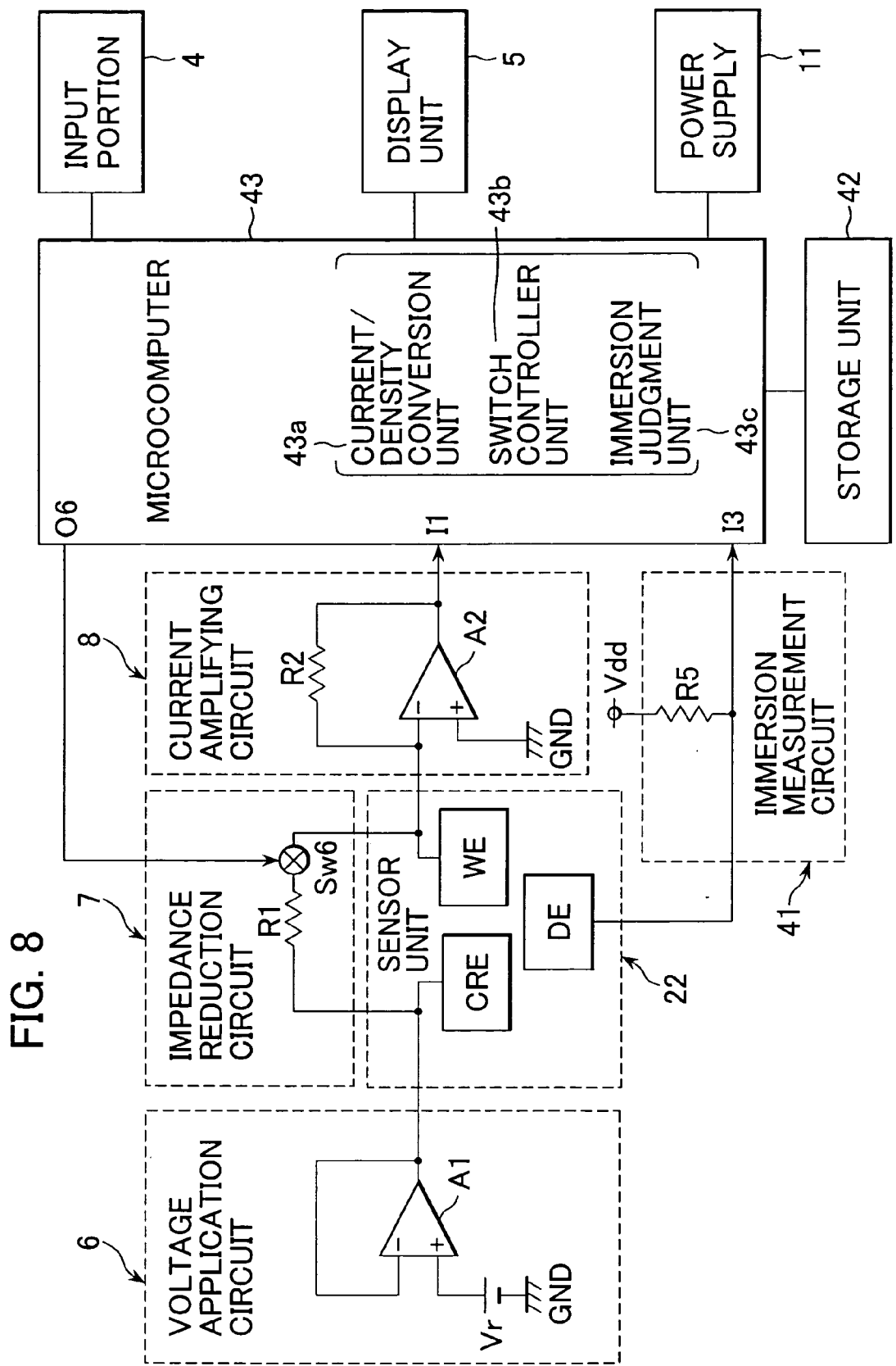
FIG. 8 is a block diagram of the polarographic densitometer (Embodiment 4)

Embodiment 4:

A polarographic densitometer according to Embodiment 4 of the present invention will be described with reference to the drawings: FIG. 1 that is an external view of the densitometer; FIG. 2 that is an enlarged view of a detector portion; FIG. 6 that is an internal view of the detector portion; and FIG. 8 that a block diagram of the densitometer.

The polarographic densitometer of this embodiment has additional components: an immersion measurement unit; and an impedance reduction circuit switching unit, both added to the configuration of Embodiment 1. Therefore, only the parts or components of the polarographic densitometer that are different from that of Embodiment 1 will be described hereafter.

The immersion measurement unit consists of a dummy electrode "DE", an immersion measurement circuit 41 and an immersion judgment circuit 43c, in order to determine whether the sensor unit is immersed in the liquid. The impedance reduction circuit switching unit includes a switch "Sw6" and a switch controller unit 43b and acts to switch the impedance reduction circuit 7 to no-connection mode for a period during which determination is done by the immersion measurement unit within the standby interval. The switch controller unit 43b and the immersion judgment circuit 43c are incorporated into a microcomputer 43, together with a current/density conversion unit 43a. A counter/reference electrode "CRE" and a working electrode "WE" added to the dummy electrode "DE" form a sensor unit 22.

Electric potential on the dummy electrode "DE" may be varied in response to any reaction with the liquid. The immersion measurement circuit includes a pull-up resistor "R5" which, together with the dummy electrode "DE", develops immersion detection potential. The switch "Sw6" acts to switch connection of the resistor "R1" between the counter/reference electrode "CRE" and the working electrode "WE". The storage unit 42 stores the predetermined voltage that is judgment criterion for determining whether the sensor unit is immersed in the liquid. The immersion judgment circuit 43c compares the immersion detection potential with the predetermined voltage for judgment criterion stored in the storage unit 42 to determine whether the end portion (the detector portion) "A" of the sensor unit 22 is immersed in the liquid. If it is determined by the immersion judgment circuit 43c that the end portion (the detector portion) "A" of the sensor unit 22 is immersed in the liquid within the standby interval then the switch controller unit 43b controls to operate the switch "Sw6" so that the resistor "R1" enters no-connection mode. On the contrary, it is determined that the end portion "A" of the sensor unit 22 is not immersed in the liquid then it controls to operate the switch "Sw6" so that the resistor "R1" enters connection mode.

Now, operation of the polarographic densitometer configured according to Embodiment 4 will be described in more detail.

When the "ON" key 4a on the device is depressed an electric power is fed from the power supply 11 to each of various components of the electrical system, and then, the device enters the standby mode. That is to say, the switch "Sw6" is turned OFF according to OFF control signal from a port "O6" of the switch controller unit 43b (i.e. the microcomputer 43) so that the resistor "R1" enters no-connection mode.

Then, any immersion detection potential on the dummy electrode "DE" is fed to the microcomputer 43 so that the immersion judgment circuit 43c compares it with the predetermined voltage for judgment criterion stored in the storage unit 42. If the immersion detection potential is not larger than the predetermined voltage for judgment criterion then it is determined that the sensor unit is not immersed in the liquid. However, If the immersion detection potential is larger than the predetermined voltage for judgment criterion then it is determined that the sensor unit is immersed in the liquid. If it is determined by the immersion judgment circuit 43c that the sensor unit is immersed in the liquid then the switch controller unit 43b makes the resistor "R1" disconnected until the "START" key 4b is depressed.

When the "START" key 4b is depressed the measurement is started. In particular, when the "START" key 4b is depressed, the specified voltage is output from the voltage follower and the switch "Sw6" is turned ON according to ON control signal from the port "O6" of the switch controller unit 43b i.e. the microcomputer 43), which makes the resistor "R1" connected.

Then, an electric current is produced to flow between the counter/reference electrode "CRE" and the working electrode "WE" in proportion to the density of specific material (in this embodiment, chlorine) in the liquid. Certain electric current also flows through the resistor "R1" between the counter/reference electrode "CRE" and the working electrode "WE".

Then, the electric current produced is amplified in the current amplifying circuit 8 and is fed to the microcomputer 43 for conversion into digital current signal. Thereafter, the current/density conversion unit 43a converts the digital current signal into the density of chlorine, which is displayed on the display unit 5.

In this embodiment the densitometer has such configuration that the voltage applying circuit 6 consists of the voltage follower to which the basic voltage "Vr" for the group of electrodes to only react with specific material of the liquid is input and from which the specified voltage is output, and the group of electrodes consists of the counter/reference electrode "CRE" to which the specified voltage is applied by the voltage follower and the working electrode for producing the current in response to any reaction caused in the specimen in conjunction with the counter/reference electrode "CRE". However, the densitometer may have another configuration, as described in Embodiment 2, in which the voltage applying circuit consists of the voltage follower to which the basic voltage for the group of electrodes to only react with specific material of the liquid is input and from which the specified voltage is output, and the group of electrodes consists of the reference electrode "RE" by which the reference voltage is developed in the specimen for providing the specified voltage output from the voltage applying circuit, the counter electrode "CE" to which the specified voltage output from said voltage follower is applied, and the working electrode "WE" for providing the current in response to any reaction caused in the specimen in conjunction with said counter electrode "CE".

Figure 9:
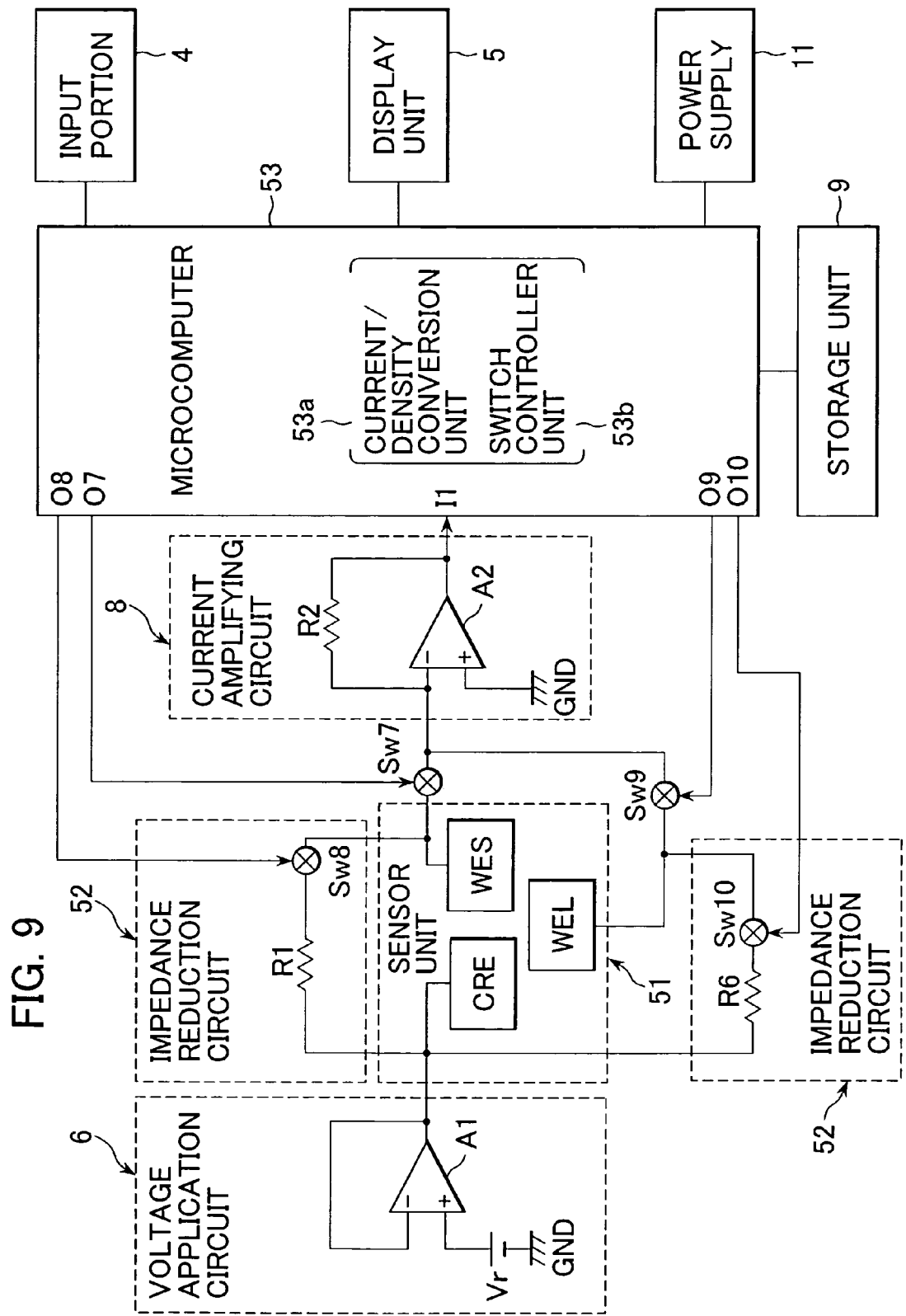
FIG. 9 is a block diagram of the polarographic densitometer (Embodiment 5)
Figure 10:
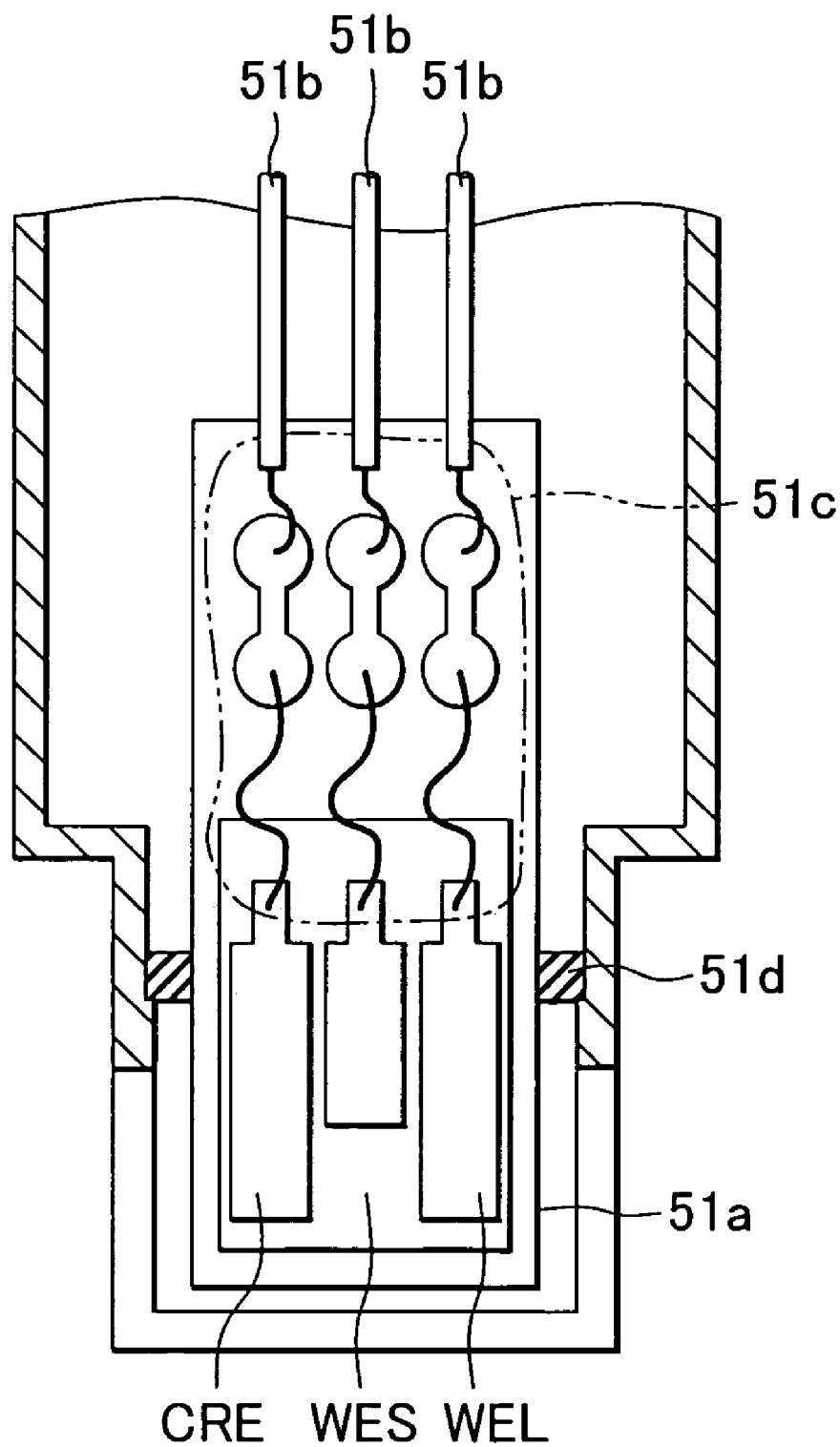
FIG. 10 is a cross-section view taken along a line B–B' in FIG. 2, illustrating an internal portion of the detector (Embodiment 5)

Embodiment 5:

A polarographic densitometer according to Embodiment 5 of the present invention will be described with reference to the drawings: FIG. 1 that is an external view of the densitometer; FIG. 2 that is an enlarged view of a detector portion; FIG. 10 that is an internal view of the detector portion; and FIG. 9 that a block diagram of the densitometer.

The polarographic densitometer of this embodiment comprises a body portion 1 having an input portion 4 (4a, 4b & 4c) and a display unit 5 both provided on the front side thereof, a sensor unit 51 having a group of electrodes (a counter/reference electrode "CRE", and a smaller working electrode "WES" and a larger working electrode "WEL") mounted therein, and a cable 3 for connecting between the body portion 1 and the sensor unit 51. The body portion 1 includes a voltage applying circuit 6, an impedance reduction circuit 52, a current amplifying circuit 8, switches "Sw7", "Sw8", "Sw9" & "Sw10", a storage unit 9 and a microcomputer 53, all mounted on an electronic board. In addition, a power supply 11 is included in the body portion 1.

The input portion 4 includes an "ON" key 4*a*, a "START" key 4*b* and a "CAL" key 4, which are used for power up, start for measurement, and calibration for the device, respectively. In particular, the "ON" key 4*a* acts to supply electric power from the power supply 11 to various components of the electrical system in the device. The "START" key 4*b* is provided for starting measurement, and the "CAL" key 4*c* acts to enter the device into calibration mode.

The display unit 5 is made up of an "LCD" and displays input condition, measurement result, calibration mode, remaining battery capacity, etc.

The sensor unit 51 includes, within an end portion (i.e. a detector portion) "A" of a rod member, a board 51*a* on which a counter/reference electrode (e.g. silver chloride) "CRE", and a smaller working electrode (e.g. platinum) "WES" and a larger working electrode (e.g. platinum) "WEL" are mounted. In addition, electric wires 51*b* extend from the electrodes through the inner portion of the rod member to the electronic board in the body portion 1. Connection between the electric wires 51*b* and the board 51*a* is covered with a water-proof and protective coating 51*c*. Furthermore, a packing 51*d* is provided for preventing any specimen (in this embodiment, liquid) from entering inside of the rod member.

The power supply 11 feeds electric power to each of various components of the electrical system.

The voltage applying circuit 6 consists of a voltage follower to which a basic voltage "Vr" for the group of electrodes (the counter/reference electrode "CRE" and the smaller and larger working electrodes "WES" & "WEL") to only react with specific material (in this embodiment, chlorine) of the specimen (in this embodiment, liquid) is input and from which the specified voltage is output.

The impedance reduction circuit 52 consists of a resistor "R1" connected between the counter/reference electrode "CRE" and the smaller working electrode "WES" as well as a resistor "R6" connected between the counter/reference electrode "CRE" and the larger working electrode "WEL" in order to reduce any impedance created between the counter/reference electrode "CRE" and the smaller working electrode "WES" as well as between the counter/reference electrode "CRE" and the larger working electrode "WEL" when they are immersed in the liquid.

An example of combination of area of the working electrode with resistance of the resistor is as follows:

Area of Working Electrode: not greater than $0.1$ mm$^2$; not less than $0.1$ mm$^2$, but not greater than $0.5$ mm$^2$; not less than $0.5$ mm$^2$, but not greater than $1.0$ mm$^2$; not less than $1.0$ mm$^2$, but not greater than $3.0$ mm$^2$; not less than $3.0$ mm$^2$, but not greater than $10.0$ mm$^2$; or not less than $10.0$ mm$^2$.

Resistance: not less than $200$ k$\Omega$; not less than $100$ k$\Omega$, but not greater than $10$ M$\Omega$; not less than $50$ k$\Omega$, but not greater than $5$ M$\Omega$; not less than $10$ k$\Omega$, but not greater than $1$ M$\Omega$; not less than $5$ k$\Omega$, but not greater than $500$ k$\Omega$; or not less than $1$ k$\Omega$, but not greater than $200$ k$\Omega$.

The current amplifying circuit 8 consists of a well known reversed type amplifier circuit for amplifying the current output which is fed from the sensor unit 51 but reduced in amplitude by the impedance reduction circuit 52.

The switches "Sw7", "Sw8", "Sw9" & "Sw10" are operated to connect or disconnect the resistor "R1" between the counter/reference electrode "CRE" and the smaller working electrode "WES" as well as the resistor "R6" between the counter/reference electrode "CRE" and the larger working electrode "WEL".

The storage unit 9 consists of an "EEPROM" in which various types of data are stored.

The microcomputer 53 has a switch controller unit 53*b* and a current/density conversion unit 53*a* incorporated therein and performs various types of operation such as conversion of analogue data acquired into digital data, calculation of density of specific material and other types of data, etc. The switch controller unit 53*b* controls operation of the switches "Sw7", "Sw8", "Sw9" & "Sw10" so that only the resistor "R1" between the counter/reference electrode "CRE" and the smaller working electrode "WES" is initially connected, but thereafter, only the resistor "R6" between the counter/reference electrode "CRE" and the larger working electrode "WEL" is connected at the time when the current measured between the counter/reference electrode "CRE" and the smaller working electrode "WES" becomes smaller than the minimum current change criterion.

The switches "Sw7", "Sw8", "Sw9" & "Sw10" and the switch controller unit 53*b* form a working electrode switching unit.

Now, operation of the polarographic densitometer configured according to Embodiment 5 will be described in more detail.

When the "ON" key 4*a* on the device is depressed an electric power is fed from the power supply 11 to each of various components of the electrical system, and then, the device enters the standby mode. Thereafter, depressing the "START" key 4*b* makes the measurement operation started. In particular, when the "START" key 4*b* is depressed the specified voltage is output from the voltage follower. Then, when the end portion (i.e. the detector portion) "A" of the sensor unit 51 is immersed in the liquid it enters inside of the end portion "A" so that the group of electrodes (the counter/reference electrode "CRE", and the smaller and larger working electrodes "WES" & "WEL") are immersed in the liquid.

Then, the switches "Sw7" & "Sw8" are turned ON according to ON control signal from the ports "O7 and "O8" of the switch controller unit 53*b* (i.e. the microcomputer 53) to make the resistor "R1" connected, while the switches "Sw9" & "Sw10" are turned OFF according to OFF control signal from the ports "O9 and "O10" of the switch controller unit 53*b* (i.e. the microcomputer 53) to make the resistor "R6" disconnected. An electric current is produced to flow between the counter/reference electrode "CRE" and the smaller working electrode "WES" in proportion to the density of specific material (in this embodiment, chlorine) in the liquid. Certain electric current also flows through the resistor "R1" between the counter/reference electrode "CRE" and the smaller working electrode "WES".

Then, the electric current produced is amplified in the current amplifying circuit 8 and is fed to the microcomputer 53 for conversion into digital current signal. The switch controller unit 53*b* compares the converted current value with the minimum current change criterion. If the comparison shows that the current value is not smaller than the minimum current change criterion then sampling of current signal is continued. However, if the current value is smaller than the minimum current change criterion then the switches "Sw7" & "Sw8" are turned OFF according to OFF control signal from the ports "O7 and "O8" of the switch controller unit 53*b* (i.e. the microcomputer 53) to make the resistor "R1" disconnected, while the switches "Sw9" & "Sw10" are turned ON according to ON control signal from the ports "O9 and "O10" of the switch controller unit 53b (i.e. the microcomputer 53) to make the resistor "R6" connected.

Then, the electric current produced is amplified in the current amplifying circuit 8 and is fed to the microcomputer 53 for conversion into digital current signal. Thereafter, the current/density conversion unit 53a converts the digital current signal into the density of chlorine, which is displayed on the display unit 5.

In this embodiment the densitometer has such configuration that the group of electrodes consists of the counter/reference electrode "CRE" to which the specified voltage is applied by the voltage applying circuit 6 and the smaller working electrode "WES" and larger working electrode "WEL" each having different area for producing the current in response to any reaction caused in the specimen in conjunction with the counter/reference electrode "CRE", the impedance reduction circuit 52 reduces the impedance in the specimen between the counter/reference electrode "CRE" and the smaller working electrode "WES" and between the counter/reference electrode "CRE" and the larger working electrode "WEL", and the working electrode switching unit acts to switch the connection of the working electrodes in such order that the smaller working electrode "WES" is initially connected and the larger working electrode "WEL" is subsequently connected. However, the densitometer may have another configuration in which the group of electrodes consists of the reference electrode "RE" by which the reference voltage is developed in the specimen for providing the specified voltage output from the voltage applying circuit, the counter electrode "CE" to which the specified voltage is applied by the voltage applying circuit, and the smaller working electrode "WES" and larger working electrode "WEL" each having different area for producing the current in response to any reaction caused in the specimen in conjunction with the counter electrode "CE", the impedance reduction circuit reduces the impedance in the specimen between the counter electrode "CE" and the smaller working electrode "WES" and between the counter electrode "CE" and the larger working electrode "WEL", and the working electrode switching unit acts to switch the connection of the working electrodes in such order that the smaller working electrode "WES" is initially connected and the larger working electrode "WEL" is subsequently connected.

Figure 12:
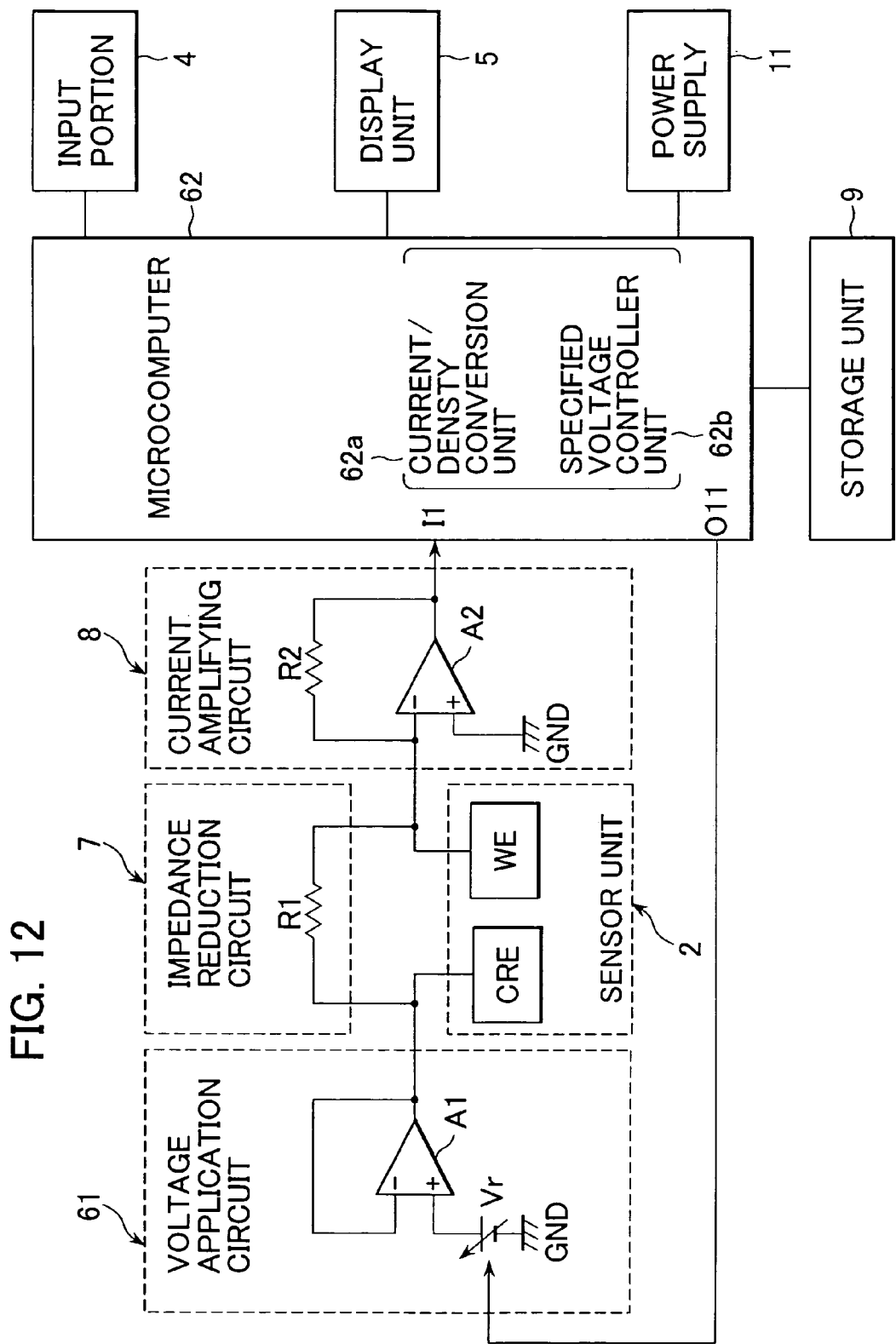
FIG. 12 is a block diagram of the polarographic densitometer.

The several embodiments of the polarographic densitometer according to the present invention have been described above, but the present invention is not limited only to those embodiments. Instead, the present invention may have many other embodiments, one of which is described below, by way of an example:

Referring to FIG. 12, a voltage applying circuit 61 is configured in such manner that variable basic voltage "Vr" is input and a plurality of specified voltage is output. Additionally, some selection unit and a specified voltage control unit 62b are provided. The selection unit includes a display unit 5, an input portion 4 and a microcomputer 62 so that any density of specific material may be selected among a plurality of densities. In particular, a plurality of specific material in the specimen is displayed on the display unit 5 and selection of the specific material desired to be measured is done by the input portion 5 under the control of the microcomputer 62. The specified voltage control unit 62b is incorporated into the microcomputer 62 and provides variable control of the basic voltage "Vr" for producing such specified voltage from the voltage applying circuit 61 that causes reaction of the group of electrodes with the specimen in proportion to the density of specific material selected by the selection unit. The polarographic densitometer config-ured in such manner can measure a plurality of specific material in the specimen so that it can find wider application and provide much usefulness in the art.

Figure 11:
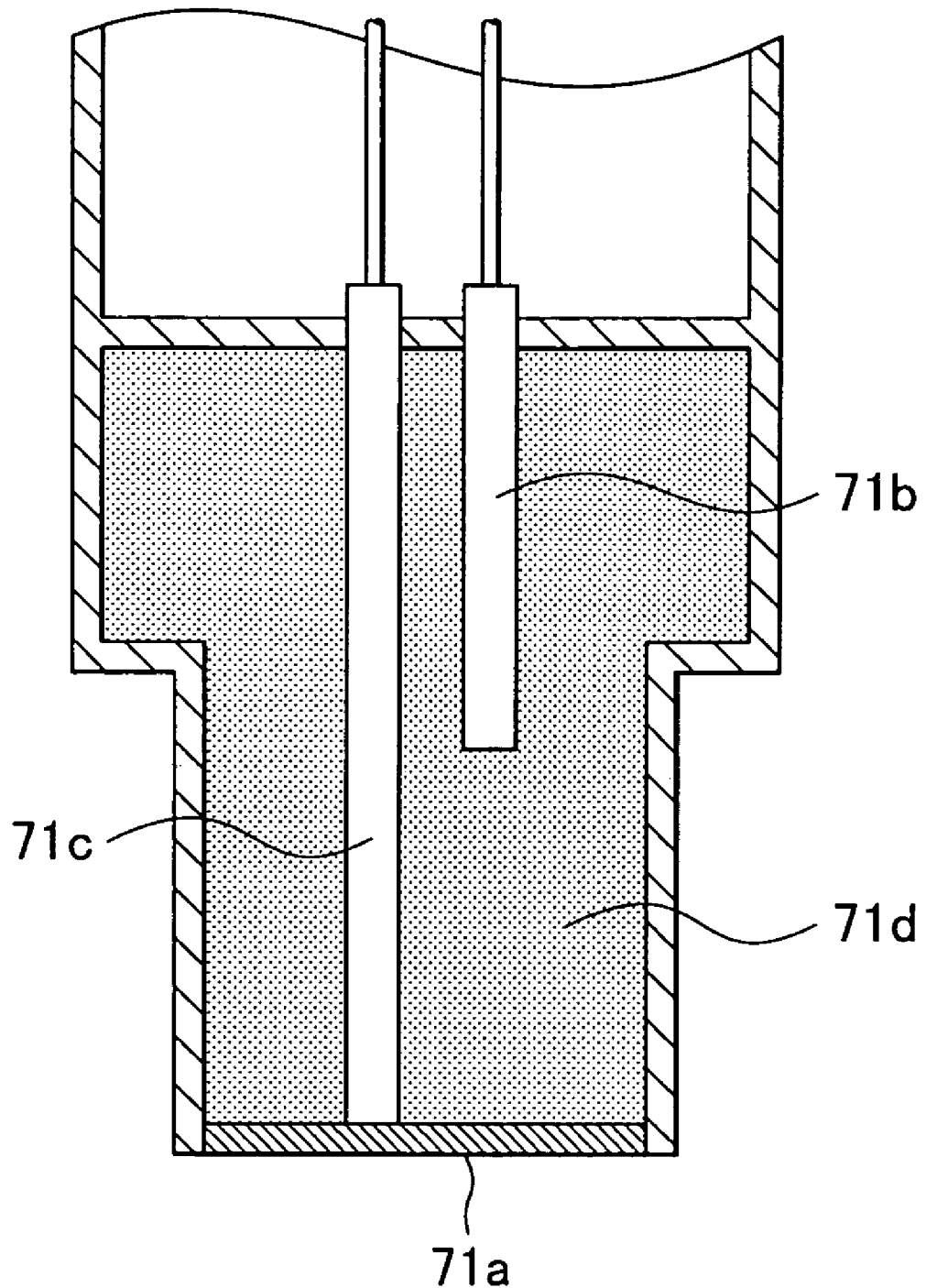
FIG. 11 is a cross-section view taken along a line B–B' in FIG. 2, illustrating an internal portion of the detector in case where specimen is gas.
Figure 15A:
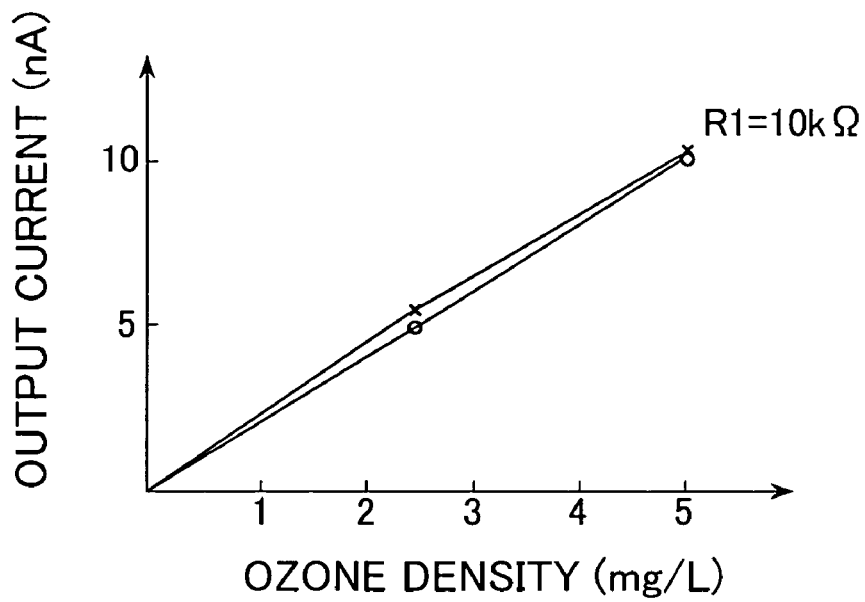
FIGS. 15A and 15B are graphs each illustrating any effect on performance (linearity) of the device due to the impedance reduction circuit (i.e. the resistor) in case where specimen is gas.
Figure 15B:
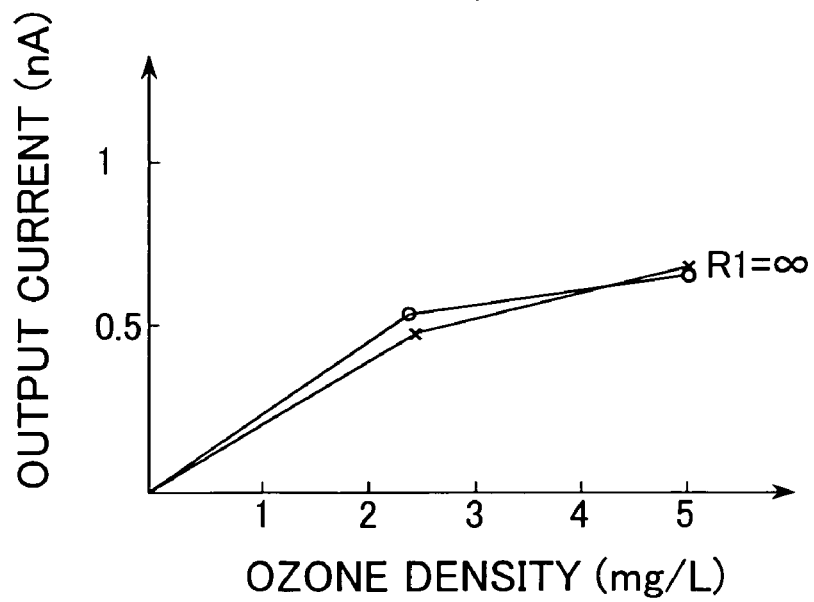

In each of the above-mentioned embodiments the specimen has been described as liquid. However, if it is desired that the present invention applies to some gas specimen only slight modification is necessary in which an end portion (i.e. a detector portion) of a sensor unit consists of a diaphragm (i.e. a gas permeable membrane) 71a, a counter/reference electrode (silver and silver chloride) 71c, a working electrode (platinum) 71b, and potassium chloride 71d, as can be seen in FIG. 11 that illustrates an internal portion of the detector. Even in case where the specimen is gas, as can be seen in FIG. 15 which is a graph illustrating relation between the current output of the sensor unit plotted on the ordinate and the ozone density plotted on abscissa, the performance of the device when the impedance reduction circuit is connected (resistor "R1"=10 k$\Omega$) is greater than that when no such circuit is connected (resistor "R1"=$\infty$), which is same as the case where the specimen is liquid, as shown in FIG. 14.

In each of the above-mentioned embodiments the impedance reduction circuit has been described as configured only by the resistor. However, any other configuration by which any impedance between electrodes can be reduced may be used.

What is claimed is:

1. A polarographic densitometer, comprising: a voltage applying circuit; a sensor unit; an impedance reduction circuit; and a current/density conversion unit, wherein said voltage applying circuit applies specified voltage, said sensor unit includes a group of electrodes to produce a current output in response to any reaction caused in a specimen when the specified voltage is applied by said voltage applying circuit, said impedance reduction circuit reduces impedance of the specimen between said electrodes of the group to stabilize the reaction caused in the specimen, and said current/density conversion unit converts the current output of said sensor unit when the impedance is reduced by said impedance reduction circuit into the density of specific material in the specimen.

2. A polarographic densitometer according to claim 1 in which if the specimen is liquid the densitometer further comprises an electric conductivity measurement unit, said conductivity measurement unit measures the electric conductivity of the liquid specimen between any of electrodes of the group, and said current/density conversion unit converts the current output of said sensor unit in proportion to the electric conductivity measured by said electric conductivity measurement unit into the density of specific material in the liquid specimen.

3. A polarographic densitometer according to claim 1 in which if the specimen is liquid the densitometer further comprises:

an immersion measurement unit; and an impedance reduction circuit switching unit, wherein said immersion measurement unit determines that said sensor unit is immersed in the liquid between any of the electrodes of the group within a standby interval before said current/density conversion unit starts to convert the current output into the density of specific material, and the impedance reduction circuit switching unit switches the impedance reduction circuit to no-connection mode for a period during which determination is done by said immersion measurement unit within the standby interval.

4. A polarographic densitometer according to claim 2 in which if the specimen is liquid the densitometer further comprises:
an immersion measurement unit; and
an impedance reduction circuit switching unit, wherein
said immersion measurement unit determines that said sensor unit is immersed in the liquid between any of the electrodes of the group within a standby interval before said current/density conversion unit starts to convert the current output into the density of specific material, and
the impedance reduction circuit switching unit switches the impedance reduction circuit to no-connection mode for a period during which determination is done by said immersion measurement unit within the standby interval.

5. A polarographic densitometer according to any one of claims 1 to 3 or 4 in which said group of electrodes consists of a counter/reference electrode to which the specified voltage is applied by said voltage applying circuit and a plurality of working electrodes each having different area to produce the current in response to any reaction caused in the specimen in conjunction with said counter/reference electrode,
said impedance reduction circuit reduces the impedance of the specimen between said counter/reference electrode and each of said working electrodes, and
a working electrode switching unit is provided for switching the connection of the plurality of working electrodes in such order that the working electrode having the smallest area is initially connected.

6. A polarographic densitometer according to any one of claims 1 to 3 or 4 in which said group of electrodes consists of a reference electrode by which a reference voltage is developed in the specimen for providing the specified voltage output from said voltage applying circuit, a counter electrode to which the specified voltage output from said voltage applying circuit is applied, and a plurality of working electrodes each having different area to produce the current in response to any reaction caused in the specimen in conjunction with said counter/reference electrode,
said impedance reduction circuit reduces the impedance of the specimen between said counter electrode and each of said working electrodes, and
a working electrode switching unit is provided for switching the connection of the plurality of working electrodes in such order that the working electrode having the smallest area is initially connected.

7. A polarographic densitometer according to any one of claims 1 to 3 or 4 in which said voltage applying circuit includes a voltage follower to which a basic voltage for said group of electrodes to only react with specific material of the specimen is input and from which the specified voltage is output, and
said group of electrodes consists of a counter/reference electrode to which the specified voltage is applied from the output of said voltage follower and a working electrode for providing the current in response to any reaction caused in the specimen in conjunction with said counter/reference electrode.

8. A polarographic densitometer according to any one of claims 1 to 3 or 4 in which said voltage applying circuit includes a voltage follower to which a basic voltage for said group of electrodes to only react with specific material of the specimen is input and from which the specified voltage is output, and
said group of electrodes consists of a reference electrode by which a reference voltage is developed in the specimen for providing the specified voltage output from said voltage applying circuit, a counter electrode to which the specified voltage output from said voltage follower is applied, and a working electrode for providing the current in response to any reaction caused in the specimen in conjunction with said counter electrode.

9. A polarographic densitometer according to any one of claims 1 to 3 or 4 in which said voltage applying circuit includes a potentiostat to which a basic voltage for said group of electrodes to only react with specific material of the specimen and a reference voltage developed in the specimen are input and from which the specified voltage is output, and
said group of electrodes consists of a reference electrode by which a reference voltage is developed in the specimen for providing the specified voltage output from said voltage applying circuit, a counter electrode to which the specified voltage output from said potentiostat is applied, and a working electrode for providing the current in response to any reaction caused in the specimen in conjunction with said counter/reference electrode.

10. A polarographic densitometer according to any one of claims 1 to 3 or 4 in which it further comprises an offset current calibration unit, said calibration unit calibrates any offset current that may be caused when the specified voltage is applied by said voltage applying circuit.

11. A polarographic densitometer according to any one of claims 1 to 3 or 4 in which it further comprises:
a current amplifier circuit; and
an amplifying factor control unit, wherein
said current amplifier circuit amplifies the current output from the sensor when the impedance is reduced by said impedance reduction circuit, and
said amplifying factor control unit controls the amplifying factor for the current from said current amplifier circuit.

12. A polarographic densitometer according to any one of claims 1 to 3 or 4 in which said voltage applying circuit applies the specified voltage that is variable, and the densitometer further comprises:
a selection unit; and
a specified voltage controller unit, wherein
said selection unit selects any density of specific material from among a plurality of densities, and
said specified voltage controller unit provides variable control to produce such specified voltage from said voltage applying circuit that causes reaction of said group of electrodes with the specimen in proportion to the density of specific material selected by said selection unit.

* * * * *